US008715677B2

(12) United States Patent
Bartlett et al.

(10) Patent No.: US 8,715,677 B2
(45) Date of Patent: May 6, 2014

(54) IMMUNOLOGICAL USES OF IMMUNOMODULATORY COMPOUNDS FOR VACCINE AND ANTI-INFECTIOUS DISEASE THERAPY

(75) Inventors: Justin B. Bartlett, Warren, NJ (US); George W. Muller, Bridgewater, NJ (US); Peter H. Schafer, Randolph, NJ (US); Christine Galustian, Croydon Surrey (GB); Angus G. Dalgleish, Cheam (GB); Brendan Meyer, London (GB)

(73) Assignee: Celgene Corporation, Summit, NJ (US)

( * ) Notice: Subject to any disclaimer, the term of this patent is extended or adjusted under 35 U.S.C. 154(b) by 714 days.

(21) Appl. No.: 11/514,447

(22) Filed: Aug. 31, 2006

(65) Prior Publication Data

US 2007/0048327 A1 Mar. 1, 2007

Related U.S. Application Data

(60) Provisional application No. 60/712,823, filed on Sep. 1, 2005.

(51) Int. Cl.
*A61K 39/00* (2006.01)

(52) U.S. Cl.
USPC ..................................... 424/184.1; 424/277.1

(58) Field of Classification Search
USPC ..................... 514/323, 417; 424/208.1; 435/4
See application file for complete search history.

(56) References Cited

U.S. PATENT DOCUMENTS

| 5,723,283 | A * | 3/1998 | Classen .............................. 435/4 |
| 6,281,230 | B1 * | 8/2001 | Muller et al. .................. 514/323 |
| 2003/0096841 | A1 * | 5/2003 | Robarge et al. ................ 514/323 |
| 2004/0022810 | A1 * | 2/2004 | Rudenko et al. ........... 424/208.1 |

FOREIGN PATENT DOCUMENTS

| WO | WO9011764 | 10/1990 |
| WO | WO9313772 | 7/1993 |
| WO | WO0145750 | 6/2001 |
| WO | WO02059106 | 8/2002 |
| WO | WO03024354 | 3/2003 |
| WO | WO2004078928 | 9/2004 |
| WO | WO2004103274 | 12/2004 |
| WO | WO2005007190 | 1/2005 |

OTHER PUBLICATIONS

Kaech et al., "Effector and Memory T-cell Differentiation: Implications for Vaccine Development." Nature Reviews Immunology 2002:v2;251-262.*
Bartlett et al., *British Journal of Cancer*, 90: 955-961 (2004).
Bielekova et al., *The Journal of Immunology*, 164: 1117-1124 (2000).
Cavanagh et al., *Int. J. Cancer*, 70: 98-105 (1997).
Corral et al., *The Journal of Immunology*, 163: 380-386 (1999).
Davies et al., *Blood*, 98: 210-216 (2001).
Dredge et al., *Critical Reviews in Immunology*, 22(5&6): 425-437 (2002).
Dredge et al., *Cancer Immunol. Immunother.*, 51: 521-531 (2002).
Dredge et al., *The Journal of Immunology*, 168: 4914-4919 (2002).
Gollob et al., *J. Clin. Invest.*, 102(3): 561-575 (1998).
Haslett et al., *The Journal of Infectious Diseases*, 187: 946-955 (2003).
Marriott et al., *Clin. Exp. Immunol.*, 130: 75-84 (2002).
Marriott et al., *Expert Opin. Biol. Ther.*, 1(4): 1-8 (2001).
Schafer et al., *The Journal of Pharmacology and Experimental Therapeutics*, 305: 1222-1232 (2003).
Schey et al., *Journal of Clinical Oncology*, 22(16): 1-8 (2004).
Galustian et al., "Lenalidomide (Revlimid®, CC-5013) and Actimid™ (CC-4047) inhibit the function and expansion of T regulatory (Treg) cells in vitro: Implications for anti-tumor activity in vivo," *Proc. Am. Assoc. Cancer Res. Ann. Meeting*, 47:1147, Abstract No. 4882 (XP001248611), (2006).
Tsenova et al., *Antimicrobial Agents and Chemotherapy*, 46(6): 1887-1895 (2002).

* cited by examiner

*Primary Examiner* — Walter Webb
(74) *Attorney, Agent, or Firm* — Jones Day

(57) ABSTRACT

Methods of enhancing immune response to an immunogen in a subject are disclosed. Also disclosed are methods of reducing the sensitivity to an allergen in a subject. The methods comprise the administration of an immunomodulatory compound in specific dosing regimens that result in enhanced immune response or reduced sensitivity.

15 Claims, 21 Drawing Sheets

List of Vaccines

| Product or trade name | Antigen(s) | Manufacturer (country) |
|---|---|---|
| A.D.T | Diphtheria, tetanus (adsorbed) | Commonwealth (Australia) |
| A.K.D.S. | Diphtheria, tetanus, pertussis | |
| AC Vax | Meningococcus (polysaccharide) | GSK (U.K.) |
| Acel-Imune [x] | Diphtheria, tetanus, (acellular) pertussis | WYE (U.S.) |
| ACTAce1 | Diphtheria, tetanus, pertussis, Hib | AVP (Argentina) |
| ActHIB | Haemophilus influenzae type b (PRP-T) | AVP (U.S.) |
| Aimmugen | Hepatitis A (inactivated) | Chemo-Sero-Therapeutic ReshInst (Japan) |
| Aldiana | Diphtheria (absorbed) | Sevac (Czechoslovakia) |
| Alditeana | Diphtheria, tetanus (absorbed) | Sevac (Czechoslovakia) |
| Alditerpera | Diphtheria, tetanus (adsorbed), pertussis | Sevac (Czechoslovakia) |
| Amaril | Yellow fever | AVP (France) |
| AMC | *Haemophilus influenzae*, type b | |
| Anadifterall | Diphtheria (adsorbed) | CHIR (Italy) |
| Anatetall | Tetanus (adsorbed) | CHIR (Italy) |
| Arilvax | Yellow fever | MEDI (U.K.) |
| Attenuvax [x] | Measles (live, further attenuated) | MRK (U.S.) |
| AVAC-1, AVA | Anthrax | |
| AVAXIM | Hepatitis A | |
| B-CAPSA [x] | *Haemophilus influenzae* type b (polysaccharide, 1987 to 1989) | Mead Johnson (U.S.) |
| BayGam | Human immunoglobulin | Bayer Corporation (U.S.) |
| BayHep B | Hepatitis B immune globulin (human) | Bayer Corporation (U.S.) |
| BayRab | Rabies immune globulin | Bayer Corporation (U.S.) |
| BayTet | Tetanus immune globulin (human) | Bayer Corporation (U.S.) |
| BCG | Tuberculosis | Multiple manfacturers and countries |
| Begrivac | Influenza (split virus) | CHIR (Germany) |
| Biavax II [x] | Rubella, mumps (live) | MRK (U.S.) |
| Biavax [x] | Rubella, mumps (live) | MRK (U.S.) |
| BIG | Botulism immune globulin (not a vaccine) | |
| Biken-HB | Hepatitis B (recombinant) | BIK (Japan) |
| Bimmugen | Hepatitis B (recombinant, adsorbed, yeast derived) | Chemo-Sero-Therapeutic Resh Inst (Japan) |

FIG. 1

| Product or trade name | Antigen(s) | Manufacturer (country) |
|---|---|---|
| BioThrax | Anthrax (adsorbed) | BPT (U.S.) |
| Biviraten Berna | Measles, mumps (live) | BER (Switzerland) |
| BVAC | Botulinum antitoxin | (for U.S. military use) |
| C.D.T. | Diphtheria, tetanus (pediatric, adsorbed) | Commonwealth (Australia) |
| Celluvax | Pertussis (acellular) | CHIR (Italy) |
| Cendevax [x] | Rubella (live) 3/70 to 1976 | RIT/SmithKline & French (U.S.) |
| Certiva [x] | Diphtheria, tetanus, (acellular) pertussis | Baxter Hyland (U.S.) |
| Cocquelucheau | Pertussis (adsorbed) | AVP (France) |
| Comvax | Hepatitis B, *Haemophilus influenza* type b | MRK (U.S.) |
| Daptacel | Diphtheria, tetanus, (acellular) pertussis | AVP (U.S.) |
| D.S.D.P.T. | Diphtheria, tetanus, pertussis (adsorbed) | Dong Shin Pharm (Korea) |
| D.T. Bis Rudivax | Diphtheria, tetanus, rubella | AVP (France) |
| Di Te Per Pol Impfstoff | Diphtheria, tetanus, pertussis, polio | BER (Switzerland) |
| Di-Te-Pol | Diphtheria, tetanus, polio | Statens Seruminstitut (Denmark) |
| Dif-Tet-All | Diphtheria, tetanus | CHIR (Italy) |
| DIFTAVAX | Diphtheria, tetanus, polio | |
| DiTe Anatoxal | Diphtheria, tetanus (adsorbed) | BER (Switzerland) |
| Ditoxim | Diphtheria, tetanus (adsorbed) | Dong Shin Pharm (Korea) |
| Double Anigen B.I. | Diphtheria, tetanus | Bengal Immunity Co (India) |
| Dryvax | Smallpox | WYE (U.S.) |
| DT | Diphtheria, tetanus (for pediatric use) | AVP (U.S.) |
| DT [x] | Diphtheria, tetanus (for pediatric use) | WYE (U.S.) |
| DT TAB | Diphtheria, tetanus, *Salmonella typhi, Paratyphi* A & B | AVP (France) |
| DTaP (generic) | Diphtheria, tetanus, (acellular) pertussis | AVP, WYE, GSK (U.S.) |
| DTwP (generic) [x] | Diphtheria, tetanus, (whole-cell) pertussis | AVP, WYE, GSK (U.S.) |
| Dual Antigen SII | Diphtheria, tetanus (adsorbed) | Serum Institute of India (India) |
| Ecolarix [x] | Measles, rubella (live) | RIT/SmithKline (U.S.) |
| eIPV | Polio (inactivated, enhanced potency) | AVP (U.S.) |
| Engerix-B | Hepatitis B | GSK (U.K., U.S.) |
| Epaxal Berna | Hepatitis A - virosomal vaccine | BER (Switzerland) |
| Ervevax RA 27/3 | Rubella (live) | GSK (Belgium) |
| Flu Shield [x] | Influenza | WYE (U.S.) |

FIG.1 (Cont.)

| Product or trade name | Antigen(s) | Manufacturer (country) |
|---|---|---|
| Fluad, Agrippal-S I | Influenza | CHIR (Italy) |
| FluMist | Influenza (live, attenuated, intranasal) | MEDI (U.S.) |
| Fluogen | Influenza | PD (U.S.) |
| Fluvirin | Influenza | EVN (U.S.) |
| Fluzone | Influenza | AVP (U.S.) |
| Funed-CEME | Diphtheria, tetanus, pertussis | Belo Horizonte (Brazil) |
| GenHevac B Pasteur | Hepatitis B | |
| Gunevax | Rubella | CHIR (Italy) |
| Havrix | Hepatitis A | GSK (U.K., U.S.) |
| H-BIG | Hepatitis B immune globulin | NABI, Bayer Corporation (U.S.) |
| HbOC | Chemical abbreviation for HibTITER | WYE (U.S.) |
| HBY | Hepatitis B (recombinant) | KGC (Japan) |
| Heprecomb | Hepatitis B (yeast derived) | BER (Switzerland) |
| Heptavax B [x] | Hepatitis B (plasma-derived) 1982 to | MRK (U.S.) |
| Hevac B | Hepatitis B (plasma derived) | AVP (France) |
| Hexavac | Diphtheria, tetanus, pertussis, polio, hepatitis B, Hib | AVP (Europe) |
| HibTITER | Haemophilus influenzae type b (HbOC) | WYE (U.S.) |
| Hinkuys karokoe | Pertussis (adsorbed) | Natl. Public Health Institute (Finland) |
| HPV-77; DK-5 | Rubella (live) 1969-1979 | MRK (U.S.) |
| HPV-77; DK-12 | Rubella (live) 19704973 | MRK (U.S.) |
| HRIG | Rabies immune globulin | AVP; Bayer Corporation (U.S.) |
| Humotet-anti Tetanus | Tetanus | Wellcome (U.K.) |
| Hyper-Tet (now called "BayTet") | Tetanus immune globulin | Bayer Corporation (U.S.) |
| IBV | Polio (inactivated) | Statens Seruminstitut (Denmark) |
| Immune Globulin Intramuscular (Human) | Broad-spectrum immune globulins | MA, BPT, New York Blood Ctr, Bayer Corporation, CEN (U.S.) |
| Imogam Rabies - HT | Rabies immune globulin | AVP (U.S.) |
| Imovax | Rabies | AVP (U.S.) |
| Imovax Parotiditis | Mumps | AVP (France) |
| Imovax Polio | Polio | AVP (France) |
| Imovax Sarampion | Measles | AVP (France) |
| Imovax D.T. | Diphtheria, tetanus | |

FIG.1 (Cont.)

| Product or trade name | Antigen(s) | Manufacturer (country) |
|---|---|---|
| Imovax Gripe | Influenza | |
| Imovax R.O.R. | Measles, rubella, mumps (live) | AVP (France) |
| Imovax Rubeola | Measles | AVP (International) |
| Imovax Mumps | Mumps | |
| Imovax Oreilions | Mumps | AVP (France) |
| Imovax Rabies I.D. | Rabies vaccine (HDCV) | AVP (U.S.) |
| Imovax Rabies I.M. | Rabies vaccine (HDCV) | AVP (U.S.) |
| Infanrix | Diphtheria, tetanus, (acellular) pertussis | GSK (Belgium, U.S.) |
| Ipad TP | Tetanus, polio | AVP (France) |
| IPOL | Polio (enhanced potency, inactivated) | AVP (U.S.) |
| IPV | Polio (inactivated) | General term for inactivated polio vaccine |
| Istivac | Influenza | |
| JE-VAX | Japanese encephalitis | AVP (U.S.) |
| Kaksoisrokote Dubbelvaccin | Diphtheria, tetanus (adsorbed) | Natl. Public Health Institute (Finland) |
| Kikhoste-Vaksine | Pertussis | *Statens Institutt for* Folkehelse *(Norway)* |
| Lancy Vaxina [x] | Smallpox | Swiss Serum and Vaccine Institute (Switzerland) |
| Lavantuu tirokote | Typhoid | Central Pub Health Lab (Finland) |
| Liovax [x] | Smallpox | CHIR (Italy) |
| Lirubel [x] | Measles, rubella (live) 4/74 to 6/78 | Dow/PitneyMoore (U.S.) |
| Lirugen | Measles | AVP ant' I) |
| Lirugen [x] | Measles (live) 2/65 to 6/78 | Dow (U.S.) |
| LM - 3 RIT | Measles, mumps, rubella (live) | Dong Shin Pharm (Korea) |
| LM - 2 RIT | Measles, mumps (live) | Dong Shin Pharm (Korea) |
| LTEANAS Imuna | Tetanus (adsorbed) | Imuna sp. (Slovakia) |
| LYMErix [x] | Lyme disease | GSK (U.S.) |
| Lyovac Attenuvax [x] | Measles (live, attenuated) | IVIRK (U.S.) |
| Lyovac Meruvax [x] | Rubella (live) | MRK (U.S.) |
| *M-R Vax II* [x] | Measles, rubella (live) | MRK (U.S.) |
| M-Vax [x] | Measles (live) 5/63 to 1979 | WYE (U.S.) |
| Masern-Impfstoff SSW | Measles (live) | |
| Measles Vaccine DK3 [x] | Measles (live) 1964 to 1972 | Philips Roxane, Inc. (U.S.) |

FIG.1 (Cont.)

| Product or trade name | Antigen(s) | Manufacturer (country) |
|---|---|---|
| Measles [x] | Measles (inactivated) 1963 to 1966<br>Measles (live) 12/64 to 1974 | Eli Lilly (U.S.) |
| Mencevax A | Meningococcus (polysaccharide) (Group A) | SmithKline/RIT (Belgium) |
| Meningitec | Meningococcus (conjugate) (Group C) | WYE (U.K., Australia) |
| Menomune-A/C/Y/W-135 | Meningococcus (polysaccharide) (Groups A,C, Y, W435) | AVP (U.S.) |
| Menpovax 4 | Meningococcus (polysaccharide) (Groups A & C) | CHIR (Italy) |
| Menpovax A+C | Meningococcus (Groups A & C) | CHIR (Italy) |
| Meruvax [x] | Rubella (live) 6/69 to | MRK (U.S.) |
| Meruvax II | Rubella (live) | MRK (U.S.) |
| Mevilin-L [x] | Measles (live) | Glaxo Operations |
| MMR [x] | Measles, mumps, rubella (live) 6/71 to | (U.S.) |
| MMR (generic) [x] | Measles, mumps, rubella (live) 4/74 to 6178 | Dow Chemical (U.S.) |
| M-M-R II | Measles, mumps, rubella (live) | MRK (U.S.) |
| Moniarix | Pneumococcal (polysaccharide) | SmithKline/RIT (Belgium) |
| Mopavac Sevac | Measles, mumps attenuated (live, ) | Institute of Sera and vaccines Czechoslovakia |
| MOPV [x] | Polio (live, Sabin, monovalent types I, II, III) | WYE (U.S.) |
| Morbilvax | Measles (live, attenuated) | CHIR (Italy) |
| Morubel | Measles, rubella (live, attenuated) | CHIR (Italy) |
| Moruman Berne | Measles immunglobulin | BER (Switzerland) |
| Morupar | Measles, mumps, rubella (live, attenuated) | CHIR (Italy) |
| Movivac | Measles (live, attenuated) | |
| M-R VAX [x] | Measles, rubella (live) 7/71 to | MRK (U.S.) |
| Mumaten Berne | Mumps (live) | BER (Switzerland) |
| Mumps (generic) [x] | Mumps (live) 4/74 to 6178 | Dow Chemical (U.S.) |
| Mumps (generic) [x] | Mumps (inactivated)1950 to 1978 | WYE (U.S.) |
| Mumps (generic) [x] | Mumps (inactivated)1950 to 1977 | Eli Lilly (U.S.) |
| Mumpsvax [x] | Mumps (live) | MRK (U.S.) |
| Mutagrip | Influenza | |
| Nabi-HB | Hepatitis B immune globulin | NABI (U.S.) |
| Nothav | Hepatitis A | CHI (Italy) |
| OmniHIB [x] | *Haemophilus influenzae* type b (PRP-T) | GSK, AVP (U.S.) |
| OPV | General term for oral polio vaccine | |

FIG. 1 (Cont.)

| Product or trade name | Antigen(s) | Manufacturer (country) |
|---|---|---|
| Orimune [x] | Polio vaccine (oral, trivalent) | WYE (U.S.) |
| Pariorix | Mumps (live) | SmithKline/RIT (Belgium) |
| Pavivac-Sevac | Mumps (live) | Institute of Immunology (Croatia) |
| PCV, PCV7 | General term for pneumococcal conjugate (7-valent) | |
| Pediarix | Diphtheria, tetanus, (acellular) pertussis, hepatitis B, IPV | GSK (U.S.) |
| PedvaxHIB | *Haemophilus influenzae type b* (PRP-OMP) | MRK (U.S.) |
| Penta | Diphtheria, tetanus, (acellular) pertussis, Hib, IPV | AVP (Canada) |
| Pentacel | Diphtheria, tetanus, pertussis, polio, Hib | AVP (Canada) |
| Pentacoq | Diphtheria, tetanus, pertussis, polio, Hib | |
| PENTAct-HIB | Diphtheria, tetanus, pertussis, polio, Hib | |
| Pentavac | Diphtheria, tetanus, pertussis, polio, Hib | |
| Pentavalente | Diphtheria, tetanus, pertussis, hepatitis B, Hib | |
| Pfizer Vax-Measles K [x] | Measles (inactivated) 3/63 to 1970 | Pfizer (U.S.) |
| Pfizer Vax-Measles L [x] | Measles (live) 2/65 to 1970 | Pfizer (U.S.) |
| Pluserix | Measles, mumps, rubella | |
| Pneumovax 23 | Pneumococcal (polysaccharide) | MRK (U.S.) |
| PNU-IMUNE 23 [x] | Pneumococcal (polysaccharide) | WYE (U.S.) |
| POLIAce1 | Diphtheria, tetanus, pertussis, polio, HIB | AVP (Argentina) |
| PPV, PPV23 | General term for pneumococcal polysaccharide (23-valent) | |
| Prevnar | Pneumococcal (7-valent, conjugate) | WYE (U.S.) |
| Priorix | Measles, mumps, rubella (live) | GSK (U.K.) |
| ProHIBiT [x] | *Haemophilus influenzae type b* (PRP-D) | AVP (U.S.) |
| PRP-OMP | Chemical abbreviation for PedvaxHIB | |
| PRP-T | Chemical abbreviation for ActHIB | |
| Purivax [x] | Polio (inactivated) 1956 to 1965 | MRK (U.S.) |
| QUADRAcel | Diphtheria, tetanus, pertussis, polio | AVP (Argentina) |
| QUADRAcel/Hibest | Diphtheria, tetanus, pertussis, polio, Hib | AVP (Argentina) |
| Quadrigen [x] | DTP + polio (1959-1968) | PD (U.S.) |
| Quatro-Virelon | Diphtheria, tetanus, polio | CHI (Germany) |
| Quintuple | Diphtheria, tetanus, pertussis, Hib, Polio | GSK (Mexico) |
| R-HB Vaccine | Hepatitis B (recombinant) | Mitsubishi Chem Corp (Japan) |

FIG.1 (Cont.)

| Product or trade name | Antigen(s) | Manufacturer (country) |
|---|---|---|
| R-VAC | Rubella (live) | Serum Institute (India) |
| RA27/3 | Rubella (live) | MRK (U.S.) |
| RabAvert | Rabies (PCEC) | CHI (U.S.) |
| Recombivax HB | Hepatitis B (recombinant) | MRK (U.S.) |
| Respigam, RSV-IVIG | Respiratory syncytial virus immune globulin (not a vaccine) | MEDI (U.S.) |
| RIG (generic) | Rabies immune globulin | Bayer Corporation, AVP (U.S.) |
| Rimevax | Measles (live) | SmithKline/RIT (Belgium) |
| Rimparix | Measles (live) | SmithKline/RIT |
| RIT - LM-2 | Measles, mumps (live) | Dong Shin Pharm (Korea) |
| MT - LM-3 | Measles, mumps, rubella (live) | Dong Shin Pharm (Korea) |
| RotaShield, RRV-TV[x] | Rotavirus -- 8/98 to 7/99 | WYE (U.S.) |
| Rouvax | Measles (live, attenuated) | AVP (France) |
| Rubeaten Berna | Rubella (live) | BER (Switzerland) |
| Rubella (generic)[x] | Rubella (live) 12/69 to 1972 | Philips Roxane (U.S.) |
| Rubellovac | Rubella | CHIR (Germany) |
| Rubelogen[x] | Rubella (live) 12/69 to 1972 | PD (U.S.) |
| Rubeovax[x] | Measles (live) 2/63 to 1971 | MRK (U.S.) |
| Rudi-Rouvax | Measles, rubella (live) | AVP (France) |
| Rudivax | Rubella (live, attenuated) | AVP (France) |
| RVA (generic) | Rabies vaccine adsorbed | BP (U.S.) |
| Sabin | General term for oral (live) polio vaccine | |
| Sahia | Polio (live, oral) | Multiple manufacturers |
| Salk | General term for injectable (inactivated) polio vaccine | |
| Sandovac | Influenza | |
| Serobacterin[x] | Pertussis — 1945 to 1954 | MRK (U.S.) |
| Sii Triple Antigen | Diphtheria, tetanus, pertussis | Serum Institute (India) |
| Stamaril | Yellow fever (live, attenuated) | AVP (France) |
| Synagis (palizivumab) | Respiratory syncytial virus immune globulin (not a vaccine) | MEDI (U.S.) |
| T. Polio | Tetanus toxoid, polio | AVP (Canada) |
| T.A.B. | Typhoid, paratyphoid (A & B) | - Institute Pasteur (Tunisia)<br>- Pharmaceutical Industries Corp. (Burma) |

FIG.1 (Cont.)

| Product or trade name | Antigen(s) | Manufacturer (country) |
|---|---|---|
| T-Immun | Tetanus (adsorbed) | |
| Td (generic) | Tetanus, diphtheria (adult formulation) | AVP, BP (U.S.) |
| Te/Vac/Ptap | Tetanus | |
| Te Anatoxal | Tetanus | BER (Europe) |
| Telvaclptap | Tetanus | |
| Tetagrip | Tetanus, influenza | AVP (France) |
| Tetamun SSW | Tetanus nonadsorbed (fluid, ) | Veb Sachsisches Serumwerk German |
| Tetamyn | Tetanus | Bioclon, S.A. De C.V. (Mexico) |
| Tetanol | Tetanus (adsorbed) | CHIR (Germany) |
| Tetasorbat SSW | Tetanus (adsorbed) | Veb Sachsisches Serumwerk (Germany) |
| Tetavax | Tetanus (adsorbed) | AVP (France) |
| Tetracoq 05 | Diphtheria, tetanus, pertussis, polio | AVP (France) |
| TetrAct-HIB | Diphtheria, tetanus, pertussis, Hib | |
| Tetramune [x] | Diphtheria, tetanus, pertussis, Hib | WYE (U.S.) |
| Tetravax [x] | Diphtheria, tetanus, pertussis, polio -1959 to 1965 | MRK (U.S.) |
| Tice BCG | Bacillus Calmette-Gudrin vaccine (for TB) | OTC (U.S.) |
| TIG | Tetanus immune globulin (generic) | Bayer Corporation (U.S.) |
| TOPV | Trivalent oral polio vaccine | Multiple manufacturers and countries |
| Titifica | Typhoid and para typhoid | |
| Tresivac Lyopholized | Measles, mumps, rubella | Serum Institute (India) |
| Triacel | Diphtheria, tetanus, (acellular) pertussis | |
| Triacelluvax | Diphtheria, tetanus, (acellular) pertussis | CHIR (Europe) |
| TriHIBit | Diphtheria, tetanus, (acellular) pertussis, Hib | AVP (U.S.) |
| Tri-Immunol [x] | Diphtheria, tetanus, pertussis | WYE (U.S.) |
| Trimovax | Measles, mumps, rubella (live) | AVP (France) |
| Trinivac [x] | Diphtheria, tetanus, pertussis – 1952 to 1964 | MRK (U.S.) |
| Tripacel | Diphtheria, tetanus, (acellular) pertussis | |
| Tripedia | Diphtheria, tetanus, (acellular) pertussis | AVP (U.S.) |
| Triple antigen | Diphtheria, tetanus, pertussis | - Chowgule & Co. (India)<br>- CSL Limited (Australia) |
| Triple Sabin | Polio (live, oral) | |
| Triple | Diphtheria, tetanus, pertussis | |

FIG.1 (Cont.)

| Product or trade name | Antigen(s) | Manufacturer (country) |
|---|---|---|
| Triple Viral | Measles, mumps, rubella | |
| Trivacuna Leti | Diphtheria, tetanus (adsorbed), pertussis | Laboratory Leti (Spain) |
| Trivax | Diphtheria, tetanus (plain), pertussis | Wellcome (U.K.) |
| Trivax-ad | Diphtheria, tetanus (adsorbed), pertussis | - EVN (UK)<br>- Wellcome (UK) |
| Trivax-Hib | Diphtheria, tetanus, pertussis, Hib | GSK (UK) |
| Trivb | Diphtheria, tetanus, pertussis | |
| Triviraten | Measles, mumps, rubella (live, attenuated) | BER (Switzerland) |
| Trivivac x | Diphtheria, tetanus, pertussis | MRK (U.S.) |
| Trivivac Sevac | Measles, mumps, rubella (live, attenuated) | Institute of Sera &Vaccines (Czechoslovakia) |
| TT | Tetanus toxoid (generic) | AVP (U.S.) |
| TT vaccine | Tetanus toxoid (adsorbed) | |
| Tussitrupin Forte | Pertussis | Staatliches Institut (Germany) |
| Twinrix | Hepatitis A & B (adult formulation) | GSK (U.K., U.S.) |
| Twinrix Junior | Hepatitis A & B (pediatric formulation) | GSK (U.S.) |
| Ty2la (Vivotif Berna) | Typhoid (live, oral, lyophilized) | BER (Switzerland) |
| Tyne | Tuberculosis (BCG) | Sweden |
| Typherix | Typhoid | GSK (U.K.) |
| Typhim Vi (ViCPs) | Typhoid (parenteral, injectable) | AVP (U.S., France) |
| Typhoid Vaccine x | Typhoid (inactivated, parenteral) | WYE (U.S.) |
| Typhopara-typhoidique | Typhoid and para typhoid | |
| VA-Mengoc-BC | Meningococcal (Groups B & C) | Finlay Vacunas y Sueros Centro de Investigation (Cuba) |
| Vaccin Difteric Adsorbit | Diphtheria toxoid (adsorbed) | Cantacuzino Institute (Romania) |
| Vaccin Combinat Diftero-Tetanic | Diphtheria, tetanus (adsorbed) | Cantacuzino Institute (Romania) |
| Vaccinum Morbillorum Vivum | Measles (live) | Moscow Research Institute (Russia) |
| Vacina Triplice Viral | Measles, mumps, rubella | |
| Vacina Triplice | Diphtheria, tetanus, pertussis | Instituto Butantan (Brazil) |
| Vacina Dupla | Diphtheria, tetanus | Instituto Butantan (Brazil) |
| Vaksin Cacar | Smallpox | |
| Vaksin Serap | Diphtheria, tetanus, pertussis | Perum Bio Farma (Indonesia) |
| Vaksin Campak Kerig | Measles (live, attenuated) | Pasteur Institute (Indonesia) |
| Vaksin Kotipa | Cholera, typhoid and paratyphoid A, B & C | Perum Bio Farina (Indonesia) |

FIG.1 (Cont.)

| Product or trade name | Antigen(s) | Manufacturer (country) |
|---|---|---|
| Vamoavax | Measles, mumps (live) | Institute of Immunology (Croatia) |
| Vaqta | Hepatitis A (inactivated) | MRK (U.S.) |
| Varicellon | Varicella zoster immunoglobulin | Behringwerke Aktiengesellschaft (Germany) |
| Varie | Smallpox (lyophilized) | Institute of Sera and Vaccine (Czechoslovakia) |
| Varilrix | Varicella (live, Oka strain) | GSK (Australia, Belgium) |
| Varivax | Varicella (live) | MRK (U.S.) |
| Vaxem-Hib | *Haemophilus influenzae* type b | CHIR (Italy) |
| Vaxicoq | Pertussis (adsorbed) | AVP (France) |
| Vaxigrip | Influenza | |
| Vaxipar | Mumps (live) | CHIR (Italy) |
| VCDT | Diphtheria, tetanus | Cantacuzino Institute (Romania) |
| VDA Vaccin Difteric Adsorb it | Diphtheria | Cantacuzino Institute (Romania) |
| ViCPs (Typhim Vi) | Typhoid (inactivated, injectable) | AVP (U.S.) |
| VIG | Variola (smallpox) immune globulin (not a vaccine) | Distributed by CDC |
| Virelon T 20 | Polio (live, oral, trivalent) | Behringserke Aktiengesellschaft (Germany) |
| Virovac Massling, Perotid, Rubella | Measles, mumps, rubella | |
| Vivotif Berna (Ty21a) | Typhoid (oral, live) | BER (Switzerland) |
| VT (Vacina Triplice) | Diphtheria, tetanus, pertussis | Instituto Butantan (Brazil) |
| VTV (Vacina Triplice Viral) | Measles, mumps, rubella | |
| VVR | Measles (live, attenuated) | Cantucuzino Institute (Romania) |
| VZIG | Varicella zoster immune globulin (generic) | MA (U.S.) |
| Welltrivax trivalente | Diphtheria, tetanus, pertussis | |
| YF-VAX | Yellow fever | AVP (U.S.) |
| Zaantide | Diphtheria anti-toxin | Inst. of Immunology (Croatia) |
| Zaantite | Tetanus anti-toxin | Inst. of Immunology (Croatia) |
| Zaditeadvax | Diphtheria, tetanus | Inst. of Immunology (Croatia) |
| Zaditevax | Diphtheria, tetanus | Inst. of Immunology (Croatia) |
| Zamevax A+C | Meningococcus (polysaccharide, Groups A & C) | Inst. of Immunology (Croatia) |
| Zamovax | Measles (live) | Inst. of Immunology (Croatia) |

FIG.1 (Cont.)

| Product or trade name | Antigen(s) | Manufacturer (country) |
|---|---|---|
| Zamruvax | Measles, rubella (live) | Inst. of Immunology (Croatia) |
| Zaruvax | Rubella (live) | Inst. of Immunology (Croatia) |
| Zatetravax | Diphtheria, tetanus, pertussis, parapertussis | Inst. of Immunology (Croatia) |
| Zatevax | Tetanus | Inst. of Immunology (Croatia) |
| Zatribavax | Diphtheria, tetanus, pertussis | Inst. of Immunology (Croatia) |
| Zatrivax | Measles, rubella, mumps (live) | Inst. of Immunology (Croatia) |

FIG. 1 (Cont.)

IMMUNOLOGICAL USES OF IMMUNOMODULATORY COMPOUNDS FOR VACCINE AND ANTI-INFECTIOUS DISEASE THERAPY

This application claims priority to U.S. provisional application No. 60/712,823, filed Sep. 1, 2005, the entirety of which is incorporated herein by reference.

1. FIELD OF THE INVENTION

This invention relates to the use of certain non-peptide small molecules known as immunomodulatory compounds or IMiDs® in various immunological applications, in particular as vaccine adjuvants, particularly anticancer vaccine adjuvants. The invention also relates to the uses of IMiDs® in combination with vaccines to treat or prevent cancer or infectious diseases. This invention also relates to other various uses of immunomodulatory compounds such as reduction or desensitization of allergic reactions.

2. BACKGROUND

2.1 Vaccines

Vaccines have traditionally consisted of live attenuated pathogens, whole inactivated organisms or inactivated toxins. In many cases, these approaches have been successful at inducing immune protection based on antibody mediated responses. However, certain pathogens, e.g., HIV, HCV, TB, and malaria, require the induction of cell-mediated immunity (CMI). Non-live vaccines have generally proven ineffective in producing CMI. In addition, although live vaccines may induce CMI, some live attenuated vaccines may cause disease in immunosuppressed subjects. As a result of these problems, several new approaches to vaccine development have emerged, such as recombinant protein subunits, synthetic peptides, protein polysaccharide conjugates, and plasmid DNA. While these new approaches may offer important safety advantages, a general problem is that vaccines alone are often poorly immunogenic. Therefore, there is a continuing need for the development of potent and safe adjuvants that can be used in vaccine formulations to enhance their immunogenicity. See, e.g., Edelman, *Molecular Biotech.* 21: 129-148 (2002); O'Hagan et al., *Biomolecular Engineering*, 18: 69-85 (2001); Singh et al., *Pharm. Res.* 19(6): 715-28 (2000) for detailed review of the state of the art in vaccine development.

Traditionally, the immunogenicity of a vaccine formulation has been improved by injecting it in a formulation that includes an adjuvant. Immunological adjuvants were initially described by Ramon (1924, *Ann. Inst. Pasteur*, 38: 1) "as substances used in combination with a specific antigen that produced a more robust immune response than the antigen alone." A wide variety of substances, both biological and synthetic, have been used as adjuvants. However, despite extensive evaluation of a large number of candidates over many years, the only adjuvants currently approved by the U.S. Food and Drug administration are aluminum-based minerals (generically called Alum). Alum has a debatable safety record (see, e.g., Malakoff, *Science*, 2000, 288: 1323), and comparative studies show that it is a weak adjuvant for antibody induction to protein subunits and a poor adjuvant for CMI. Moreover, Alum adjuvants can induce IgE antibody response and have been associated with allergic reactions in some subjects (see, e.g., Gupta et al., 1998, *Drug Deliv. Rev.* 32: 155-72; Relyveld et al., 1998, *Vaccine* 16: 1016-23). Many experimental adjuvants have advanced to clinical trials since the development of Alum, and some have demonstrated high potency but have proven too toxic for therapeutic use in humans. Thus, an on-going need exists for safe and potent adjuvants.

Cancer vaccines have been a subject of much attention. Recently, there appears to be an emerging consensus that cancer vaccines are less likely to be successful in the context of high tumor buden/load (see, e.g., *Nature Medicine Commentary*, 10(12): 1278 (2004) and *Cancer Immunol. Immunother.*, 53(10): 844-54 (2004)). This is attributed to effective tumor-mediated immune suppression due to the secretion of IL-10, TGF-b, and PGE-2, among others.

On the other hand, recent evidence suggests that immediately after tumor resection or ablation, there is leakage of tumor cells in the peripheral blood. Therefore, the presence of tumor antigen in the context of low tumor burden, without associated immune suppression, may enable re-priming of the immune response. Thus, a need exists for an agent that promotes the long-term anti-tumor immunity, possibly through Th1 type cellular immune responses.

2.2 Regulatory T Cells ($T_{reg}$ Cells)

$T_{reg}$ cells refer to a population of specialized T cells that express CD4 and CD25. $T_{reg}$ cells are exceptional in that their main function appears to be suppression of function of other cells. In this regard, $T_{reg}$ cells are also referred to as "suppressor cells." It has been reported that a further defining characteristic of $T_{reg}$ cells is their expression of the transcription factor Foxp3.

Due to the variety of their effect, $T_{reg}$ cells have been a subject of a great deal of interest. It has been reported that $T_{reg}$ cells may influence the outcome of infection, autoimmunity, transplantation, cancer and allergy. It has been suggested that the modes of suppression employed by $T_{reg}$ cells range from the cytokines IL-10 and TGF-β to cell-cell contact via the inhibitory molecule CTLA-4. Recently, it has been reported that dendritic cells (DC) may induce the activation and proliferation of $T_{reg}$ cells, although DC are recognized as powerful activators of immune response due, in part, to their potency as antigen presentation cells (APC). See Yamazaki et al., *J. Exp. Med.*, 198: 235 (2003).

Generally, it is believed that $T_{reg}$ cells suppress the immunity of the host, and thus preventing an immunogen (e.g., a vaccine) from invoking effective immune response in the host. On the other hand, the absence of $T_{reg}$ cells can lead to an outburst of immune response, often resulting in inflammation or autoimmunity. Therefore, to maximize the immunity acquired from an immunogen, a balance needs to be achieved with regard to the level or functionality of $T_{reg}$ cells.

2.3 Gamma Delta (γδ) T Cells

Human T cells bearing the γδ T cell receptor represent a unique lymphocyte population with characteristic tissue distribution, being present in organized lymphoid tissue as well as skin- and gut-associated lymphoid tissue. γδ T cells are activated in a non-MHC restricted manner by small phosphorylated non-peptidic metabolites, including the prototypic ligand isopentenyl pyrophosphate (IPP). Some γδ T cell ligands are microbial intermediates from the farnseylpyrophosphate synthesis pathway, which is ubiquitous and essential for cell survival. This unique antigen specificity has been suggested to be best suited for activation of sentinel cells independently of antigens derived from individual microbes (De Libero, *Immunology Today*, 18: 22-26 (1997)). Recent data suggest that γδ T cells play a role in tumor surveillance, for example, of spontaneous B cell lymphomas (Street et al, *J Exp Med*, 199: 879-884(2004)), since these cells have been shown to recognize intermediates of the melavonate pathway, an essential pathway leading to cholesterol biosynthesis (Gober et al, *J Exp Med*, 197: 163-168 (2003)). These γδ T cell tumor ligands can be enhanced by treatment with aminobisphosphonates (nitrogen containing bisphophoante drugs include pamidronate and zolodronate and are used in myeloma treatment), suggesting that pretreatment with these drugs could sensitize tumor cells to γδ T cell-mediated killing. γδ T cells may also be able to augment anti-tumor immunity by enhancing dendritic cell maturation (Ismaili et al, *Clin Immunol*, 103: 296-302 (2002)).

In non-cancer settings, γδ T cells play a role in protection from viral infection, e.g., West Nile virus (Wang et al, *J Immunol*, 171: 2524-2531(2003)). Also, intraepithelial γδ T cells play a protective role in intestinal inflammation (Chen et al, Proc. Natl. Acad. Sci. U.S.A., 99: 14338-14343 (2002); and Inagaki-Ohara et al, *J Immunol*, 173: 1390-1398 (2004)). Furthermore, γδ TCR-bearing dendritic epidermal cells play a role in wound repair (Jameson et al, *Science*, 296: 747-749 (2002)).

2.4 Immunomodulatory Compounds

A number of studies have been conducted with the aim of providing compounds that can safely and effectively be used to treat diseases associated with abnormal production of TNF-α. See, e.g., Marriott, J. B., er al., *Expert Opin. Biol. Ther.* 1(4):1-8 (2001); G. W. Muller, et al., *Journal of Medicinal Chemistry*, 39(17): 3238-3240 (1996); and G. W. Muller, et al., *Bioorganic & Medicinal Chemistry Letters*, 8: 2669-2674 (1998). Some studies have focused on a group of compounds selected for their capacity to potently inhibit TNF-α production by LPS stimulated PBMC. L. G. Corral, et al., *Ann. Rheum. Dis.*, 58 (suppl I): 1107-1113 (1999). These compounds, which are referred to as IMiDs® (Celgene Corporation) or Immunomodulatory Drugs, show not only potent inhibition of TNF-α but also marked inhibition of LPS induced monocyte IL1β and IL12 production. LPS induced IL6 is also inhibited by immunomodulatory compounds, albeit partially. These compounds are potent stimulators of LPS induced IL10. Id. Particular examples of IMiDs® include, but are not limited to, the substituted 2-(2,6-dioxopiperidin-3-yl)phthalimides and substituted 2-(2,6-dioxopiperidin-3-yl)-1-oxoisoindoles described and claimed in U.S. Pat. Nos. 6,281,230 and 6,316,471, both to G. W. Muller, et al.

3. SUMMARY OF THE INVENTION

This invention relates to immunological and other uses of IMiDs®. In particular, this invention encompasses the use of IMiDs® in combination of an immunogen (e.g., a vaccine) in specific dosing regimen, providing an enhanced immune responses from the immunogen as compared to the responses obtained when IMiDs® are not used.

This invention also encompasses methods of reducing or inhibiting proliferation or immuno-suppressive activity of $T_{reg}$ cells comprising contacting the $T_{reg}$ cell with an immunomodulatory compound of the invention.

This invention also encompasses methods of eliciting an enhanced immune response from an immunogen. This invention also encompasses methods of eliciting a reduced allergic response from an allergen. The methods comprise administering an immunomodulatory compound of the invention to a subject prior to the exposure of the subject to an immunogen or an allergen. It should be noted that IMiDs® can be additionally administered during and/or after the subject's exposure to the immunogen or allergen.

Pharmaceutical compositions, dosing regimen, and combination therapies using an immunomodulatory compound are also encompassed by the invention.

4. BRIEF DESCRIPTION OF FIGURES

FIG. 1 is a non-limiting list of vaccines that may be used in connection with methods of this invention.

Figures 3A, 3B, 3C:
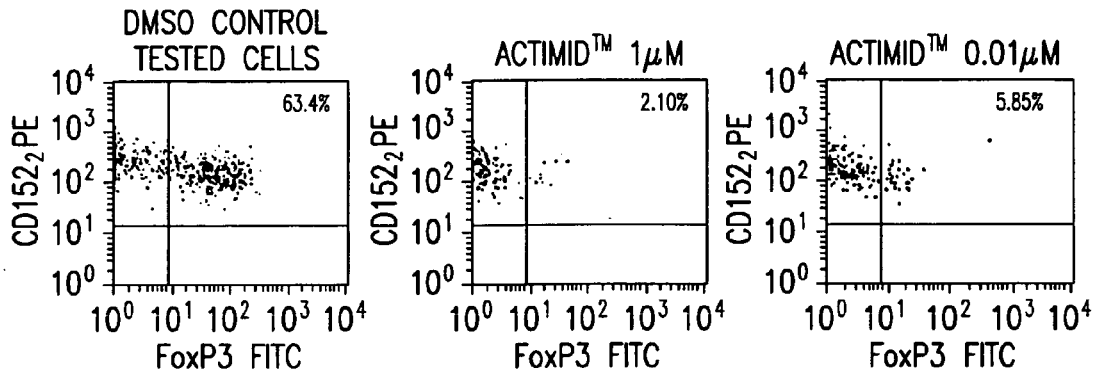
Figures 3D, 3E:
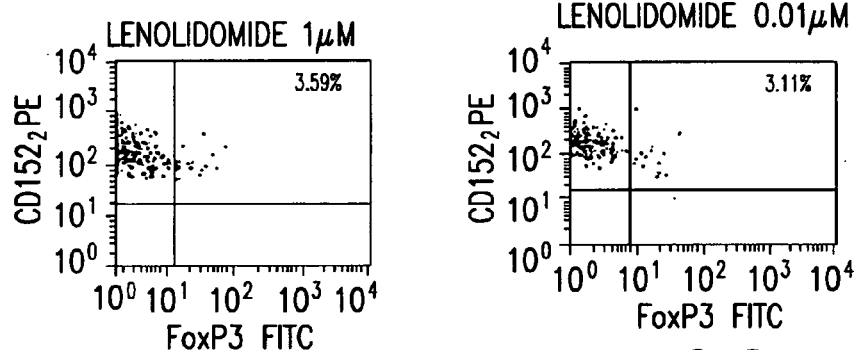
Figures 3F, 3G:
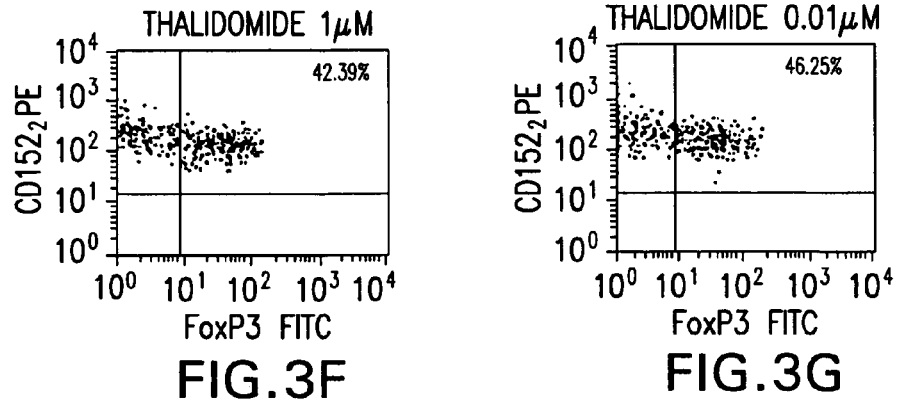

FIG. 3 illustrates the effects of immunomodulatory compounds of the invention and thalidomide on the expression of $T_{reg}$ marker Foxp3 (FIG. 3A-DMSO control; FIG. 3B-1 μM 4-(amino)-2-(2,6-dioxo(3-piperidyl))-isoindoline-1,3-dione; FIG. 3C-0.01 μM 4-(amino)-2-(2,6-dioxo(3-piperidyl))-isoindoline-1,3-dione; FIG. 3D-1 μM 3-(4-amino-1-oxo-1,3-dihydro-isoindol-2-yl)-piperidine-2,6-dione; FIG. 3E-0.01 μM 3-(4-amino-1-oxo-1,3-dihydro-isoindol-2-yl)-piperidine-2,6-dione; FIG. 3F-1 μM thalidomide; and FIG. 3G-0.01 μM thalidomide).

Figure 4:
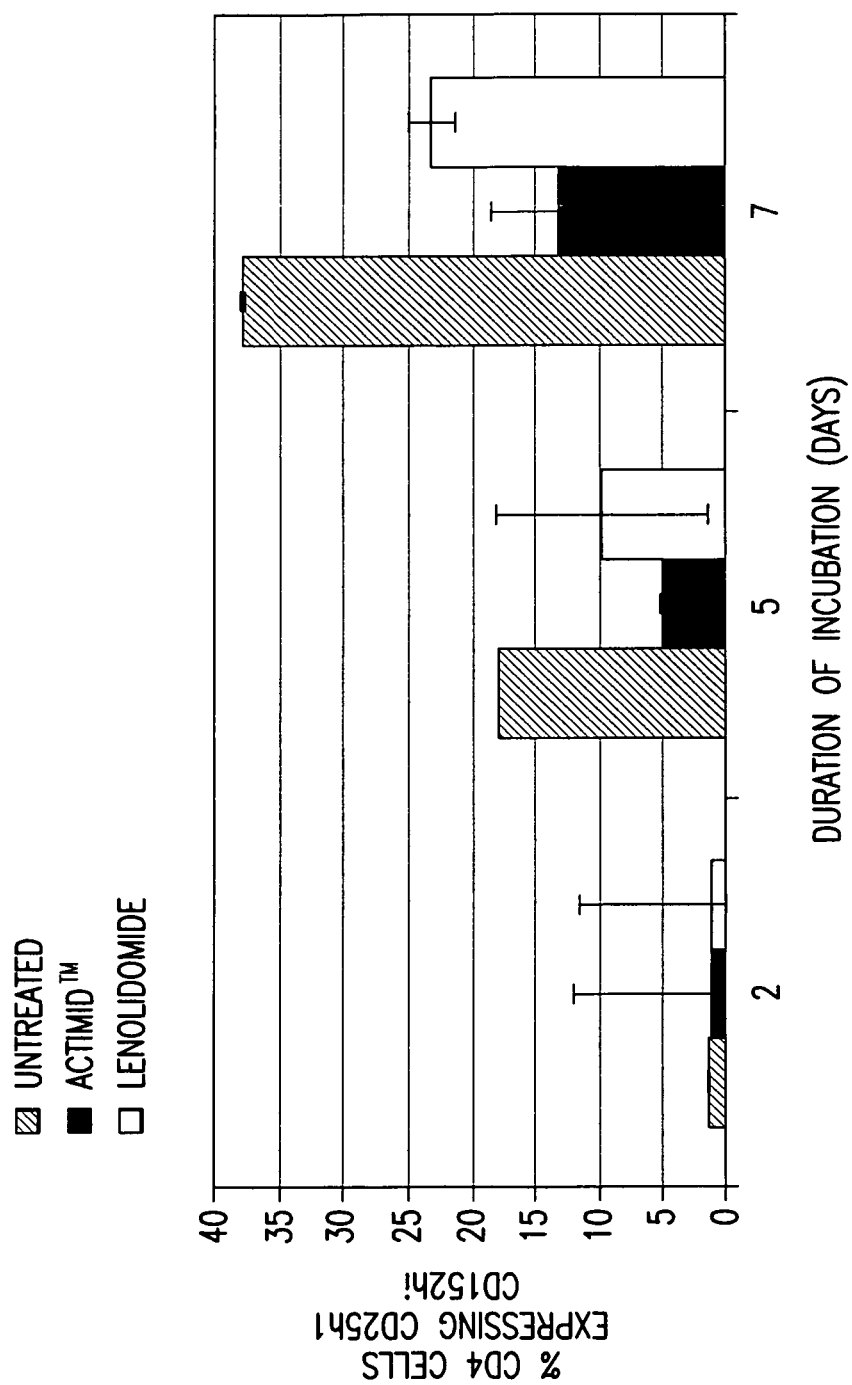

FIG. 4 illustrates the effects of 4-(amino)-2-(2,6-dioxo(3-piperidyl))-isoindoline-1,3-dione and 3-(4-amino-1-oxo-1, 3-dihydro-isoindol-2-yl)-piperidine-2,6-dione on the number of regulatory T cells.

Figure 5A:
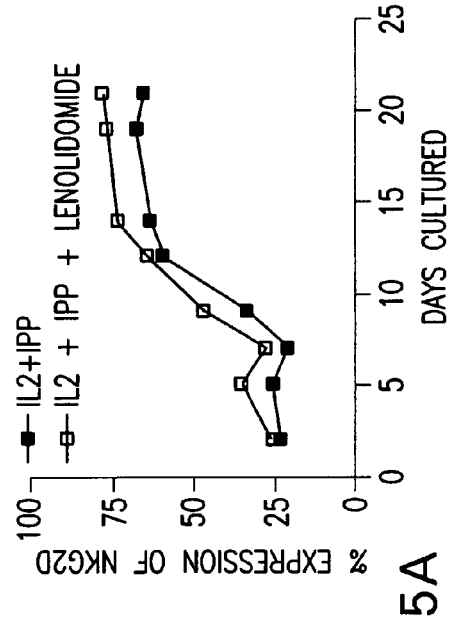

FIG. 5A illustrates the effects of 3-(4-amino-1-oxo-1,3-dihydro-isoindol-2-yl)-piperidine-2,6-dione on the expression of γδ T cells in PMBC activated with IL-2 and IPP.

Figure 5B:
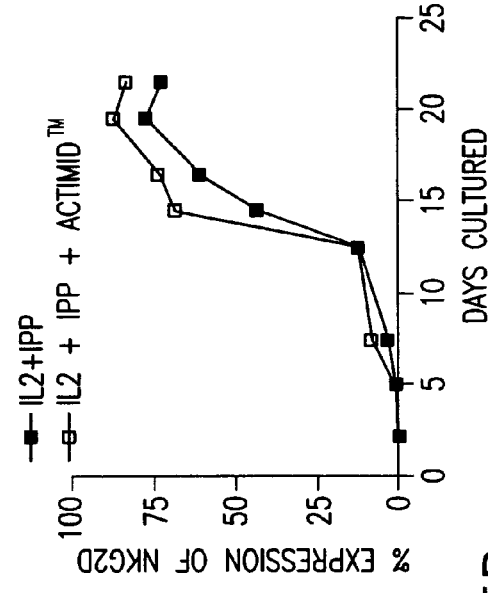

FIG. 5B illustrates the effects of 4-(amino)-2-(2,6-dioxo (3-piperidyl))-isoindoline-1,3-dione on the expression of γδ T cells in PMBC activated with IL-2 and IPP.

Figure 5C:
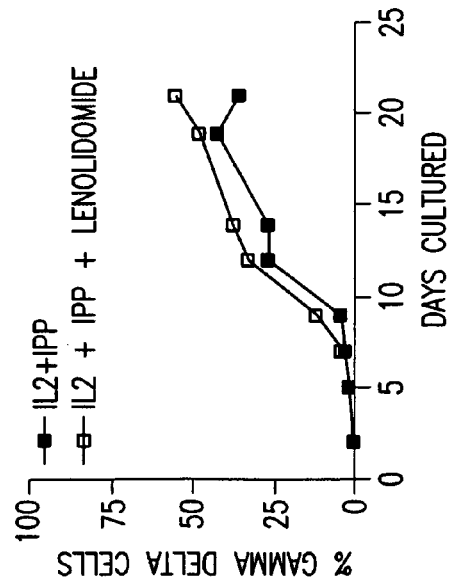

FIG. 5C illustrates the effects of 3-(4-amino-1-oxo-1,3-dihydro-isoindol-2-yl)-piperidine-2,6-dione on the expression of NKG2D in PMBC activated with IL-2 and IPP.

Figure 5D:
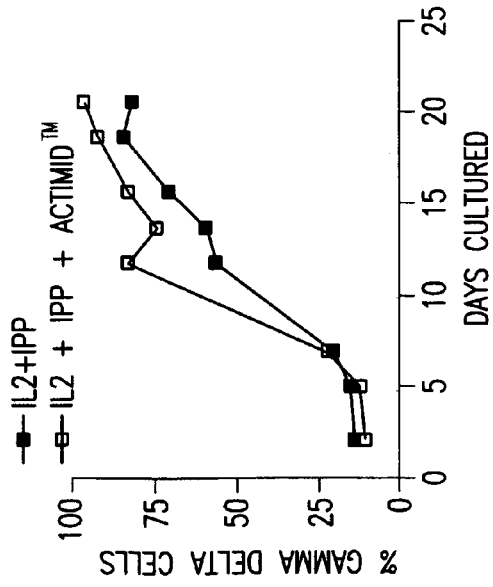
Figure 6B:
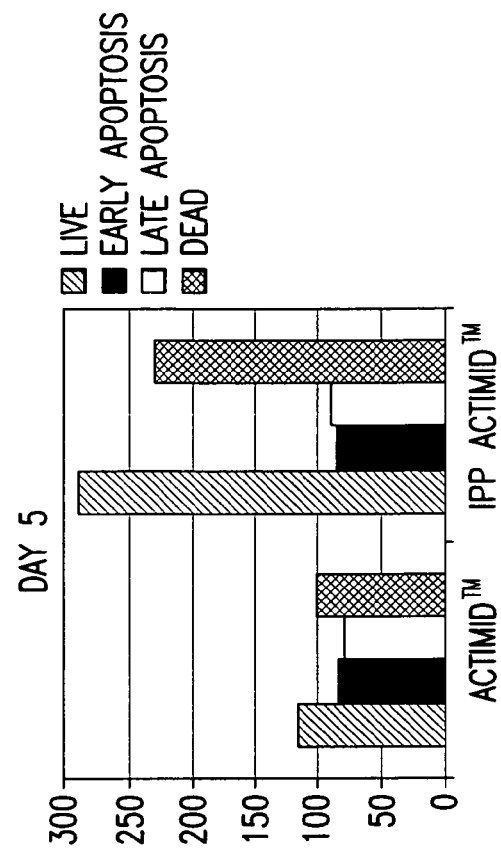
Figure 6A:
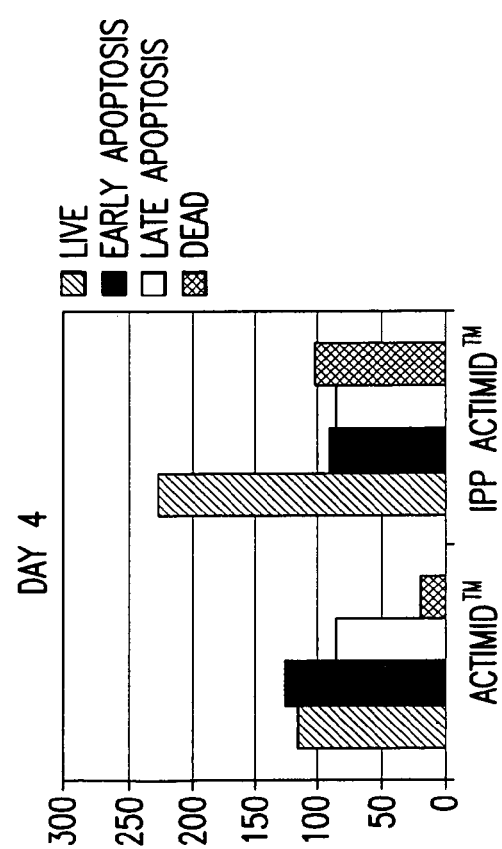
Figure 6D:
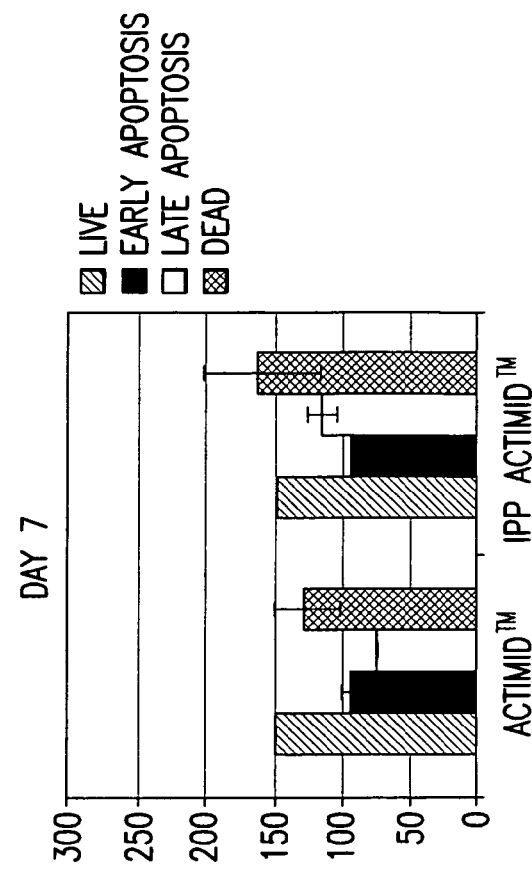
Figure 6C:
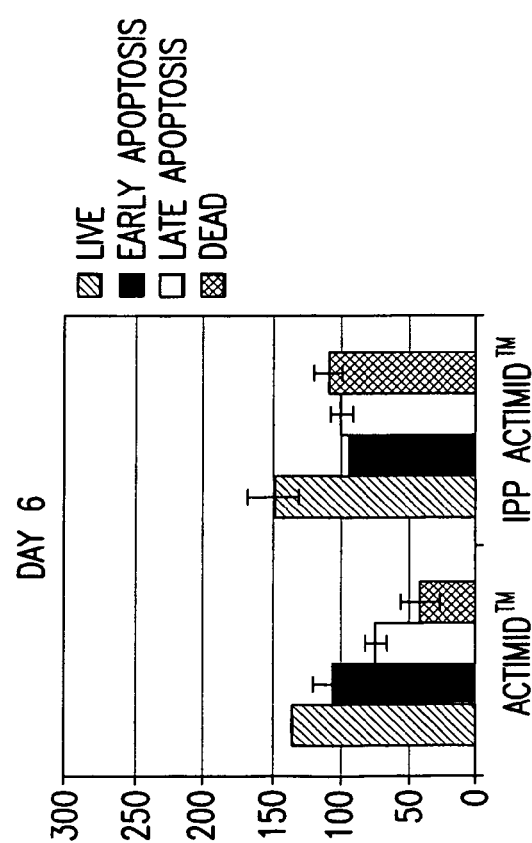

FIG. 5D illustrates the effects of 4-(amino)-2-(2,6-dioxo (3-piperidyl))-isoindoline-1,3-dione on the expression of NKG2D in PMBC activated with IL-2 and IPP.

FIG. 6 illustrates the effects of 4-(amino)-2-(2,6-dioxo(3-piperidyl))-isoindoline-1,3-dione on the apoptosis in γδ T cells on day 4 (FIG. 6A), day 5 (FIG. 6B), day 6 (FIG. 6C), and day 7 (FIG. 6D) after the treatment.

Figure 7A:
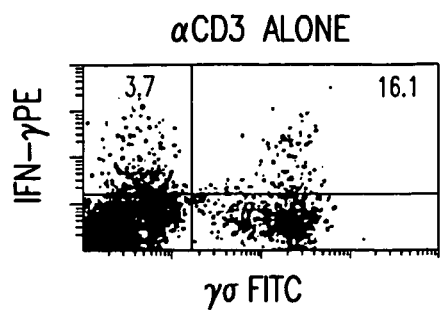
Figure 7B:
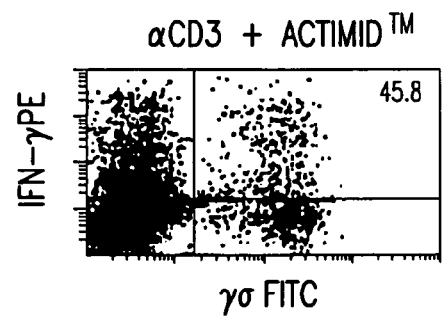

FIGS. 7A and 7B illustrate the comparison of IFN-γ production in cells treated with αCD3 alone (FIG. 7A) and those treated with αCD3 and 4-(amino)-2-(2,6-dioxo(3-piperidyl))-isoindoline-1,3-dione (FIG. 7B) in freshly prepared γδ T cells.

Figure 7C:
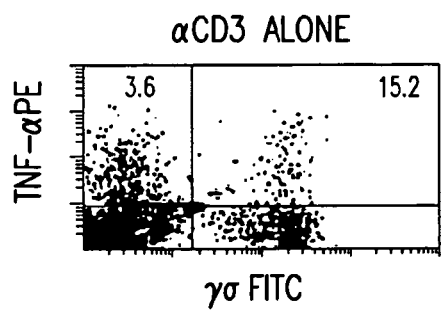
Figure 7D:
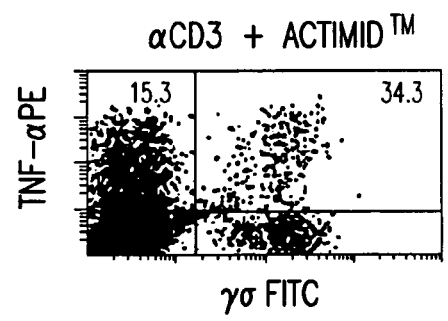

FIGS. 7C and 7D illustrate the comparison of TNF-α production in cells treated with αCD3 alone (FIG. 7C) and those treated with αCD3 and 4-(amino)-2-(2,6-dioxo(3-piperidyl))-isoindoline-1,3-dione (FIG. 7D) in freshly prepared γδ T cells.

Figure 7E:
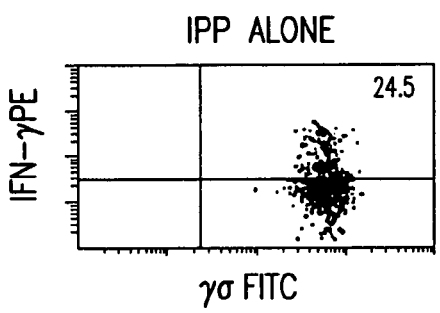
Figure 7F:
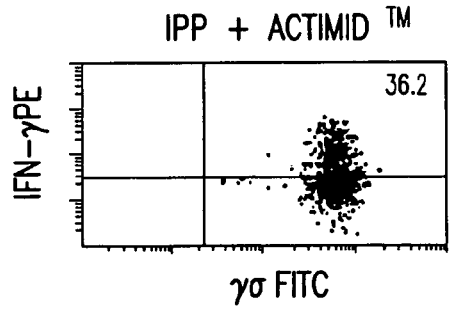

FIGS. 7E and 7F illustrate the comparison of IFN-γ production in cells treated with IPP alone (FIG. 7E) and those treated with IPP and 4-(amino)-2-(2,6-dioxo(3-piperidyl))-isoindoline-1,3-dione (FIG. 7F) in freshly prepared γδ T cells.

Figure 7G:
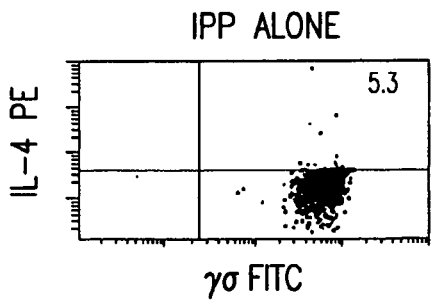
Figure 7H:
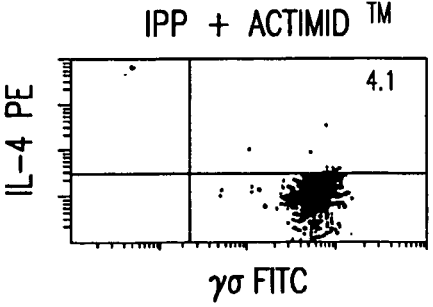

FIGS. 7G and 7H illustrate the comparison of TNF-α production in cells treated with IPP alone (FIG. 7G) and those treated with IPP and 4-(amino)-2-(2,6-dioxo(3-piperidyl))-isoindoline-1,3-dione (FIG. 7H) in freshly prepared γδ T cells.

Figure 8A:
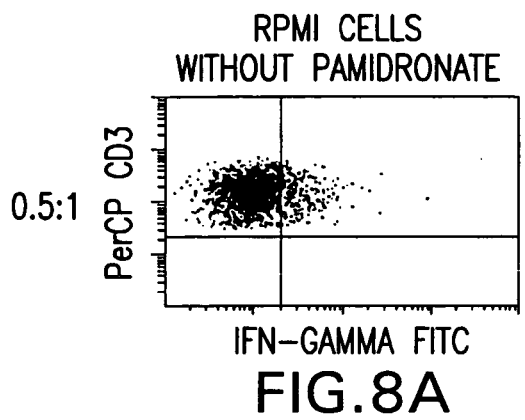

FIG. 8A illustrates the IFN-γ production in response to co-culture with RPMI cells with (tumor:γδ T=0.5:1 ratio) without preincubation with pamidronate.

Figure 8B:
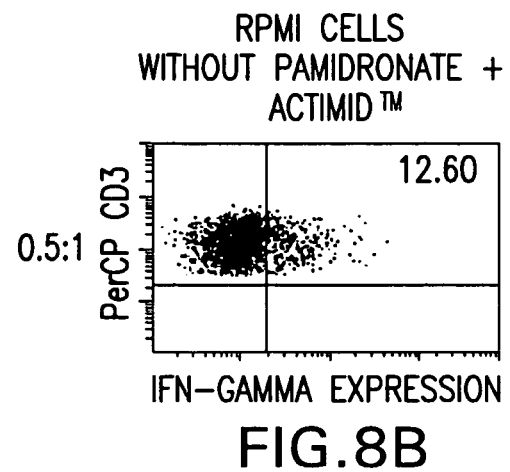

FIG. 8B illustrates the IFN-γ production in response to co-culture with RPMI cells with (tumor:γδ T=0.5:1 ratio) without preincubation with pamidronate, but with treatment with 4-(amino)-2-(2,6-dioxo(3-piperidyl))-isoindoline-1,3-dione.

Figure 8C:
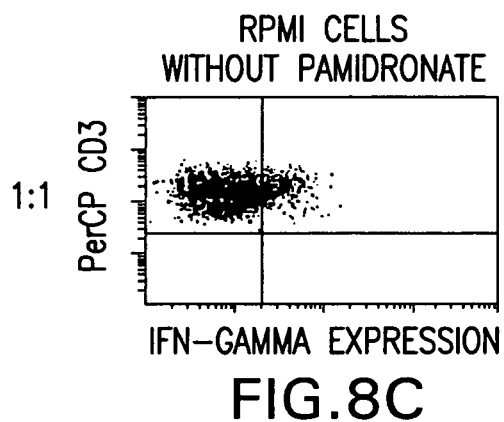

FIG. 8C illustrates the IFN-γ production in response to co-culture with RPMI cells with (tumor:γδ T=1:1 ratio) without preincubation with pamidronate.

Figure 8D:
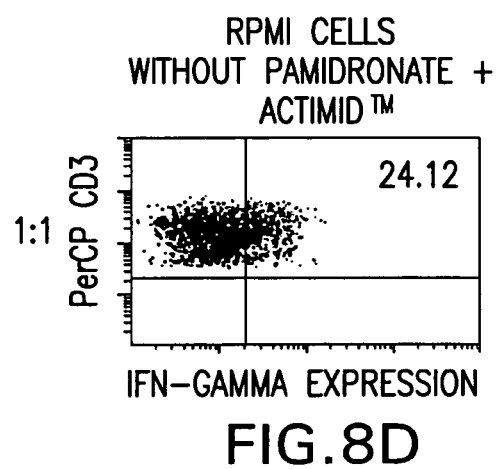

FIG. 8D illustrates the IFN-γ production in response to co-culture with RPMI cells with (tumor:γδ T=1:1 ratio) without preincubation with pamidronate, but with treatment with 4-(amino)-2-(2,6-dioxo(3-piperidyl))-isoindoline-1,3-dione.

Figure 8E:
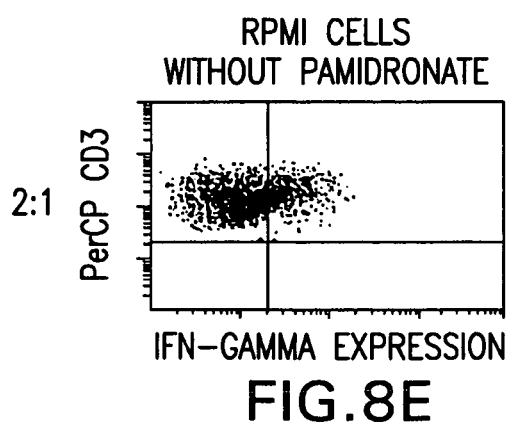

FIG. 8E illustrates the IFN-γ production in response to co-culture with RPMI cells with (tumor:γδ T=2:1 ratio) without preincubation with pamidronate.

Figure 8F:
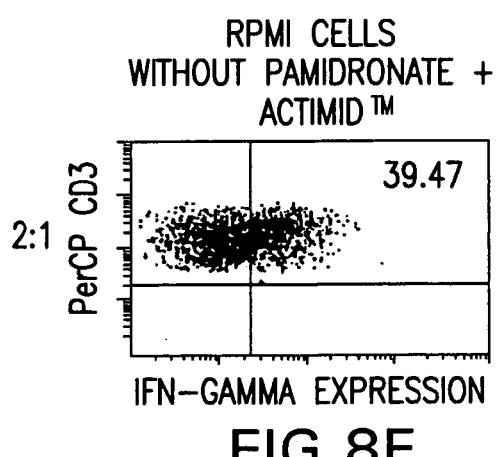

FIG. 8F illustrates the IFN-γ production in response to co-culture with RPMI cells with (tumor:γδ T=2:1 ratio) without preincubation with pamidronate, but with treatment with 4-(amino)-2-(2,6-dioxo(3-piperidyl))-isoindoline-1,3-dione.

Figure 8G:
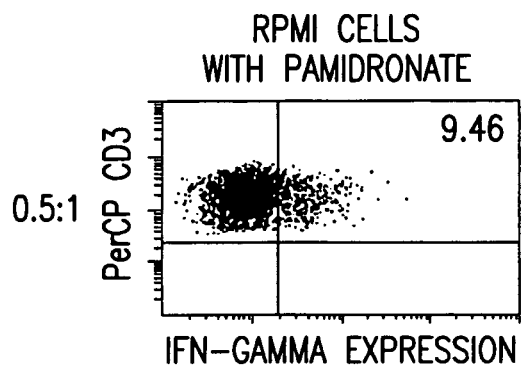

FIG. 8G illustrates the IFN-γ production in response to co-culture with RPMI cells with (tumor:γδ T=0.5:1 ratio) with preincubation with pamidronate.

Figure 8H:
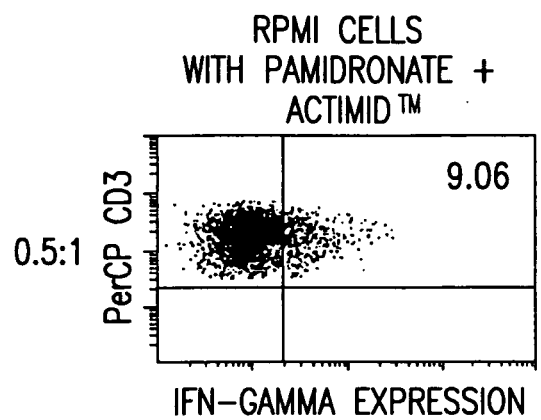

FIG. 8H illustrates the IFN-γ production in response to co-culture with RPMI cells with (tumor:γδ T=0.5:1 ratio) with preincubation with pamidronate and treatment with 4-(amino)-2-(2,6-dioxo(3-piperidyl))-isoindoline-1,3-dione.

Figure 8I:
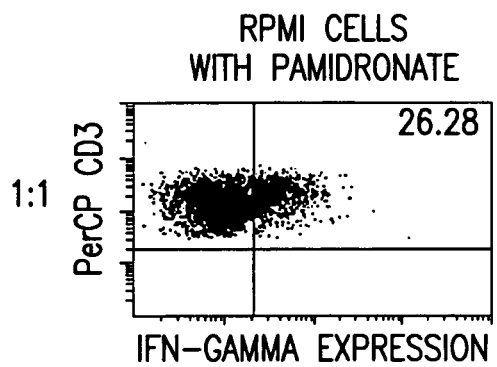

FIG. 8I illustrates the IFN-γ production in response to co-culture with RPMI cells with (tumor:γδ T=1:1 ratio) with preincubation with pamidronate.

Figure 8J:
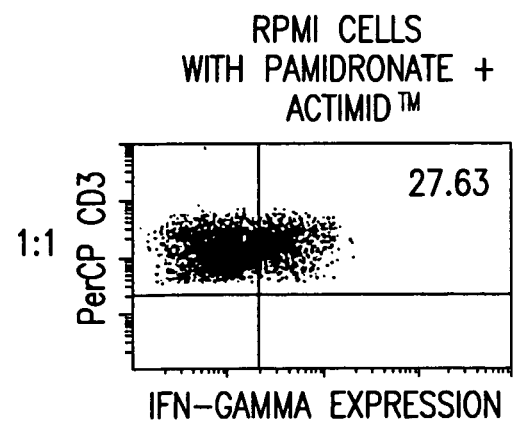

FIG. 8J illustrates the IFN-γ production in response to co-culture with RPMI cells with (tumor:γδ T=1:1 ratio) with preincubation with pamidronate and treatment with 4-(amino)-2-(2,6-dioxo(3-piperidyl))-isoindoline-1,3-dione.

Figure 8K:
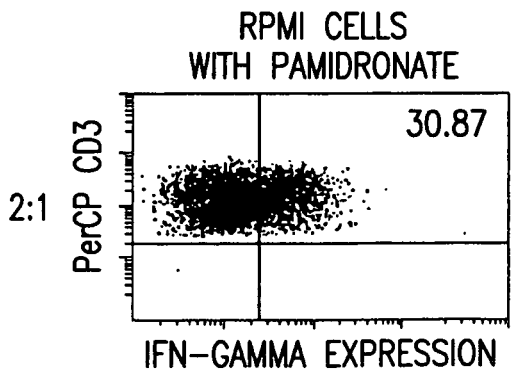

FIG. 8K illustrates the IFN-γ production in response to co-culture with RPMI cells with (tumor:γδ T=2:1 ratio) with preincubation with pamidronate.

Figure 8L:
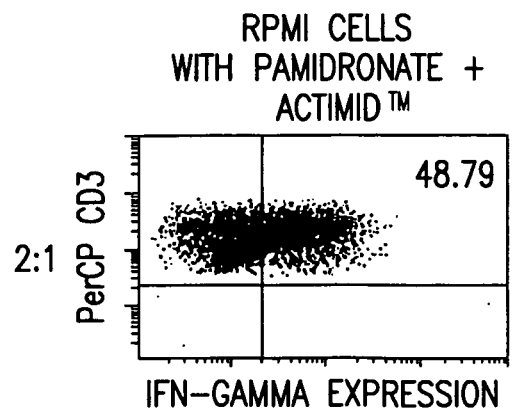

FIG. 8L illustrates the IFN-γ production in response to co-culture with RPMI cells with (tumor:γδ T=2:1 ratio) with preincubation with pamidronate and treatment with 4-(amino)-2-(2,6-dioxo(3-piperidyl))-isoindoline-1,3-dione.

Figure 9A:
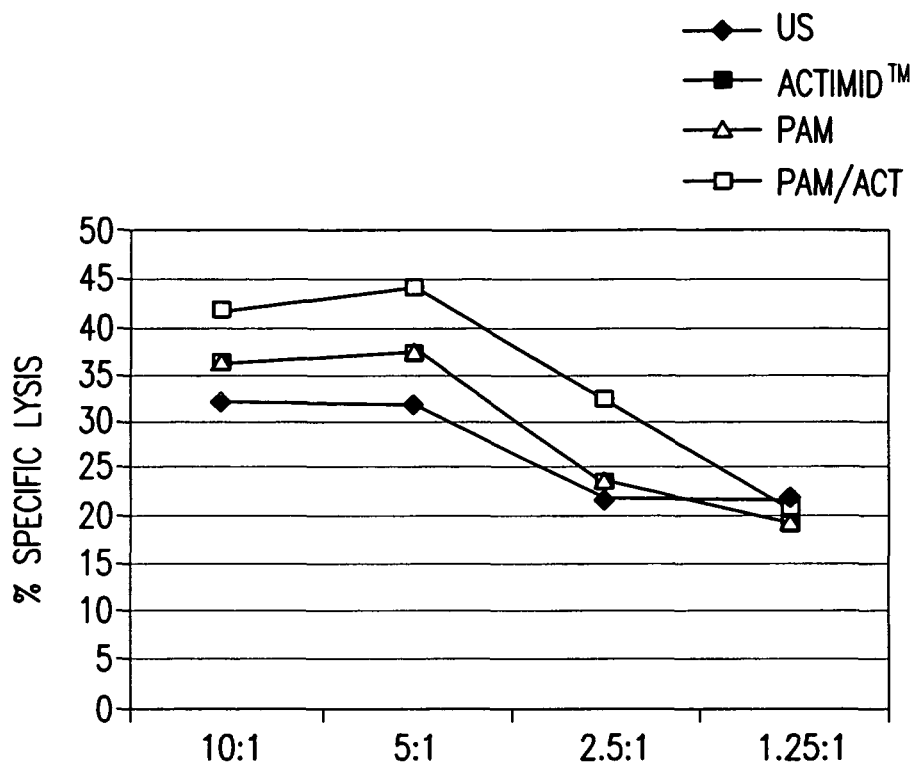

FIG. 9A illustrates the effects of immunomodulatory compounds of the invention on the cytotoxicity of γδ T cells on MM cell lines where the compounds are preincubated with tumor cells.

Figure 9B:
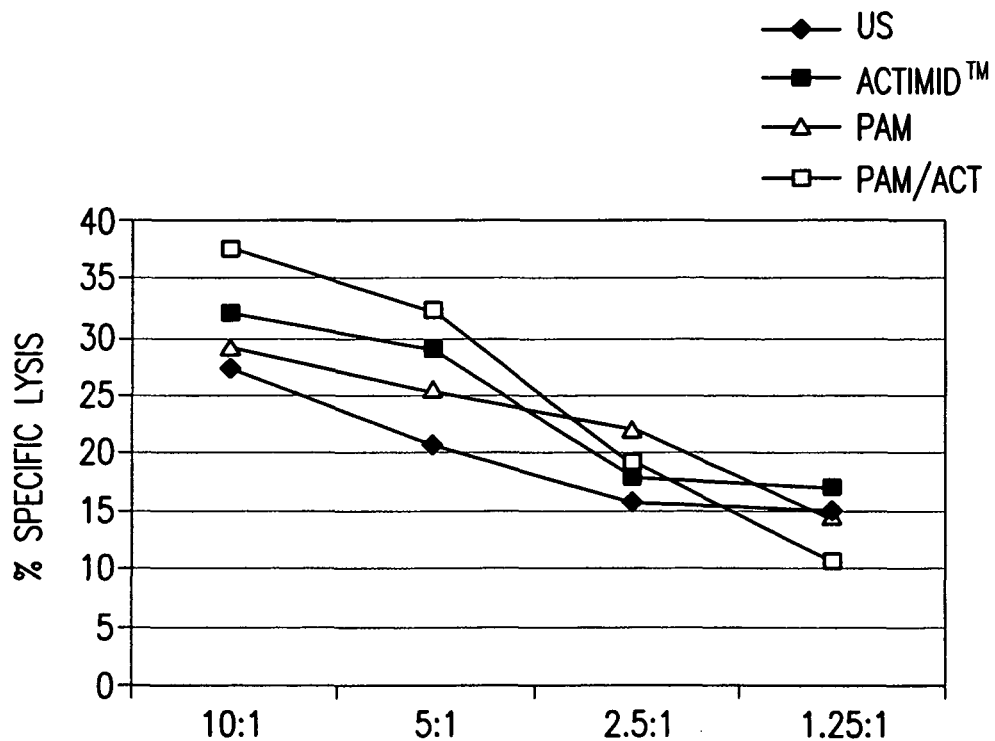

FIG. 9B illustrates the effects of immunomodulatory compounds of the invention on the cytotoxicity of γδ T cells on MM cell lines where the compounds are not preincubated with tumor cells, but are added during the chromium release assay only.

5. DETAILED DESCRIPTION OF THE INVENTION

This invention is based, in part, on the inventors' discovery that pre-treatment with immunomodulatory compounds of the invention, before the introduction of an immunogen (e.g., a vaccine) results in an enhanced immune response in a host, as determined by the experiments described herein. Without being limited by a particular theory, the invention encompasses administration of an immunomodulatory compound to a host, preferably prior to the introduction of an immunogen, to enhance the function of dendritic cells as antigen presentation cells and/or suppress the proliferation and/or function of $T_{reg}$ cells, resulting in an enhanced immune response in the host. In addition, without being limited by a particular theory, immunomodulatory compounds of the invention augment the innate anti-tumor activity of γδ T cells. Furthermore, without being limited by a particular theory, it is also believed that the immunomodulatory compounds of the invention promote successful Th1 type cellular immune responses necessary for efficient long-term anti-tumor activity, thereby delaying or prevent tumor recurrence.

Accordingly, this invention encompasses methods of reducing or inhibiting proliferation and/or immuno-suppressive activity of regulatory T cells comprising contacting the regulatory T cells with an immunomodulatory compound of the invention for a time sufficient for the reduction or the inhibition of proliferation and/or immuno-suppressive activity.

As used herein, and unless otherwise specified, the term "reducing or inhibiting the proliferation," when used in connection with regulatory T cells, means that the number of regulatory T cells in a cell culture or a host treated with an immunomodulatory compound of the invention is less than the number of regulatory T cells in a cell culture or a host without the treatment with an immunomodulatory compound of the invention, as determined by methods known in the art, some of which are described herein. A typical method involves the staining of a marker and analysis of the stain using, for example, FACS analysis. Preferably, reduced proliferation means the number of T cells in immunomodulatory compound treated culture or host is about 10%, 20%, 30%, 50%, 70%, or 90% or less than those in the culture or host without such treatment.

As used herein, and unless otherwise specified, the term "reducing or inhibiting the immuno-suppressive activity," when used in connection with regulatory T cells, means that the immuno-suppressive activity of regulatory T cells, when treated or contacted with an immunomodulatory compound of the invention, is lower than those without such treatment or contact. The immuno-suppressive activity can be determined using methods known in the art including those described herein. Typically, the immuno-suppressive activity of regulatory T cells can be assessed by monitoring the proliferation of, for example, anti-CD3 stimulated CD25− cells in response to TCR signal. Preferably, reduced immuno-suppressive activity means the activity of regulatory T cells treated with an immunomodulatory compound of the invention is about 10%, 20%, 30%, 50%, 70%, or 90% or less than the activity of those without such treatment.

This invention also encompasses methods of eliciting an enhanced immune response from an immunogen in a subject (e.g., human) comprising administering to the subject an immunomodulatory compound of the invention prior to the administration of the immunogen to the subject.

As used herein, and unless otherwise specified, the term "immunogen" means any substance or organism that provokes an immune response (produces immunity) when introduced to the body. In some embodiments, an immunogen can be used in therapeutic settings in a form of a vaccine.

As used herein, and unless otherwise specified, the term "enhanced immune response" means that, when an immunogen is administered in combination with an immunomodulatory compound according to methods of this invention, there is an increased antibody formation, measured using any standard methods known in the art or described herein, in a subject that receives such an administration as compared to a subject to which same amount of the immunogen alone is administered. As used herein, the term "administration in combination with," used in connection with two or more therapeutic agents, means that such agents are administered simultaneously, concurrently, or sequentially using the same or different routes. Preferably, an enhanced immune response means about 10%, 20%, 30%, 50%, 70%, or 100% or greater increase in antibody formation.

In specific embodiments, an immunomodulatory compound is administered to a subject about 30 days, 20 days, 15 days, 12 days, 10 days, 7 days, 5 days, 3 days, 1 day, 12 hours, or 5 hours prior to the administration of the immunogen. In other embodiments, an immunomodulatory compound is administered from about 30 days to about 5 hours, from about 20 days to about 5 hours, from about 15 days to about 12 hours, from about 12 days to about 5 hours, from about 10 days to about 12 hours, from about 7 days to about 12 hours, from about 5 days to about 12 hours, from about 5 days to about 1 day, from about 3 days to about 12 hours, or from about 3 days to about 1 day prior to the administration of an immunogen.

In other embodiments, methods of the invention further comprises a second administration of an immunomodulatory compound of the invention after the administration of an immunogen. Without being limited by a particular theory, it is believed that administering an immunomodulatory compound after the administration of an immunogen can enhance the immune response obtained from the immunogen by improving antigen presentation of host cells, enhancing the activity of T cells (e.g., $\alpha\beta$ and $\gamma\delta$ TCR positive), and generating cytotoxic effector response and long term memory (e.g., Th1 type) immune response. In these embodiments, there are at least two administrations of an immunomodulatory compound of the invention—one pre-immunogen and one post-immunogen.

In specific embodiments, an immunomodulatory compound of the invention is administered to a subject about 30 days, 20 days, 15 days, 12 days, 10 days, 7 days, 5 days, 3 days, 1 day, 12 hours, or 5 hours after the administration of the immunogen. In other embodiments, an immunomodulatory compound of the invention is administered from about 5 hours to about 30 days, from about 5 hours to about 20 days, from about 12 hours to about 15 days, from about 5 hours to about 12 days, from about 12 hours to about 10 days, from about 12 hours to about 7 days, from about 12 hours to about 5 days, from about 1 day to about 5 days, from about 12 hours to about 3 days, or from about 1 day to about 3 days after the administration of an immunogen.

In another aspect, this invention encompasses methods of eliciting a reduced allergic response in a subject comprising administering to the subject an immunomodulatory compound of the invention prior to the subject's exposure to an allergen. As used herein, the term "subject's exposure to allergen" encompasses a subject's exposure to an allergen which is foreseeable (e.g., intake of food or exposure to the naturally occurring allergens), as well as allergy vaccination where an allergen is administered to a subject according to a dosing scheme over a period of time. Without being limited by a particular theory, it is believed that immunomodulatory compounds not only preferentially induce Th1 immune response, but also inhibit and/or reverse Th2 differentiation, resulting in milder, non-acute immune response to an allergen mediated by Th1 cells.

In specific embodiments, an immunomodulatory compound is administered to a subject about 30 days, 20 days, 15 days, 12 days, 10 days, 7 days, 5 days, 3 days, 1 day, 12 hours, 5 hours, 2 hours, or 30 minutes prior to the subject's exposure to an allergen. In other embodiments, an immunomodulatory compound is administered from about 30 days to about 30 minutes, from about 20 days to about 1 hour, from about 15 days to about 1 hour, from about 12 days to about 30 minutes, from about 10 days to about 2 hours, from about 7 days to about 2 hours, from about 5 days to about 2 hours, from about 5 days to about 1 hour, from about 1 day to about 30 minutes, or from about 1 day to about 2 hours prior to the subject's exposure to an allergen.

In other embodiments, methods of the invention further comprises a second administration of an immunomodulatory compound of the invention after the subject's exposure to an allergen. Without being limited by a particular theory, it is believed that administering an immunomodulatory compound after the subject's exposure to an allergen can generate long term memory (e.g., Th1 type) immune response. In these embodiments, there are at least two administrations of an immunomodulatory compound of the invention—one pre-allergen and one post-allergen.

In specific embodiments, an immunomodulatory compound of the invention is administered to a subject about 30 days, 20 days, 15 days, 12 days, 10 days, 7 days, 5 days, 3 days, 1 day, 12 hours, or 5 hours after the subject's exposure to an allergen. In other embodiments, an immunomodulatory compound of the invention is administered from about 5 hours to about 30 days, from about 5 hours to about 20 days, from about 12 hours to about 15 days, from about 5 hours to about 12 days, from about 12 hours to about 10 days, from about 12 hours to about 7 days, from about 12 hours to about 5 days, from about 1 day to about 5 days, from about 12 hours to about 3 days, or from about 1 day to about 3 days after the subject's exposure to an allergen.

5.1 Immunogens and Vaccines

Various immunogens may be used in connection with methods of this invention. The immunogens are usually administered to a subject in a form of an immunogenic composition (e.g., a vaccine), but may be administered in any form that is acceptable for use in animals, in particular, humans.

5.1.1 Immunogens

Immunogens that may be used in the immunogenic compositions include antigens from an animal, a plant, a bacteria, a protozoan, a parasite, a virus or a combination thereof. Immunogens may be any substance that under appropriate conditions results in an immune response in a subject, including, but not limited to, polypeptides, peptides, proteins, glycoproteins, lipids, nucleic acids (e.g., RNAs and DNAs) and polysaccharides.

An immunogenic composition may comprise one or more immunogens. The amount of the immunogen used in the compositions may vary depending on the chemical nature and the potency of the immunogen.

Immunogens may be any viral peptide, protein, polypeptide, or a fragment thereof, derived from a virus.

Immunogens used in methods of the invention may be an antigen of a pathogenic virus such as, but are not limited to: adenovirdiae (e.g., mastadenovirus and aviadenovirus), herpesviridae (e.g., herpes simplex virus 1, herpes simplex virus 2, herpes simplex virus 5, and herpes simplex virus 6), leviviridae (e.g., levivirus, enterobacteria phase MS2, allolevirus), poxyiridae (e.g., chordopoxyirinae, parapoxvirus, avipoxvirus, capripoxvirus, leporipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory syncytial virus), and metapneumovirus (e.g., avian pneumovirus and human metapneumovirus), picornaviridae (e.g., enterovirus, rhinovirus, hepatovirus (e.g., human hepatitis A virus), cardiovirus, and apthovirus, reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g. human immunodeficiency virus 1 and human immunodeficiency virus 2), spumavirus), flaviviridae (e.g., hepatitis C virus), hepadnaviridae (e.g., hepatitis B virus), togaviridae (e.g., alphavirus, e.g., sindbis virus) and rubivirus (e.g., rubella virus), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus).

Immunogens used in methods of this invention may be an infectious disease agent including, but not limited to, influenza virus hemagglutinin (Genbank Accession No. J02132; Air, 1981, *Proc. Natl. Acad. Sci. USA* 78: 7639-7643; Newton et al., 1983, *Virology* 128: 495-501), human respiratory syncytial virus G glycoprotein (Genbank Accession No. Z33429; Garcia et al., 1994, *J. Virol.*; Collins et al., 1984, *Proc. Natl. Acad. Sci. USA* 81: 7683), core protein, matrix protein or any other protein of Dengue virus (Genbank Accession No. M19197; Hahn et al., 1988, *Virology* 162: 167-180), measles virus hemagglutinin (Genbank Accession No. M81899; Rota et al., 1992, *Virology* 188: 135-142), herpes simplex virus type 2 glycoprotein gB (Genbank Accession No. M14923; Bzik et al., 1986, *Virology* 155:322-333), poliovirus I VP1 (Emini et al., 1983, *Nature* 304:699), envelope glycoproteins of HIV I (Putney et al., 1986, *Science* 234: 1392-1395), hepatitis B surface antigen (Itoh et al., 1986, *Nature* 308: 19; Neurath et al., 1986, *Vaccine* 4: 34), diptheria toxin (Audibert et al., 1981, *Nature* 289: 543), *streptococcus* 24M epitope (Beachey, 1985, *Adv. Exp. Med. Biol.* 185:193), gonococcal pilin (Rothbard and Schoolnik, 1985, *Adv. Exp. Med. Biol.* 185:247), pseudorabies virus g50 (gpD), pseudorabies virus II (gpB), pseudorabies virus gIII (gpC), pseudorabies virus glycoprotein H, pseudorabies virus glycoprotein E, transmissible gastroenteritis glycoprotein 195, transmissible gastroenteritis matrix protein, swine rotavirus glycoprotein 38, swine parvovirus capsid protein, *Serpulina hydodysenteriae* protective antigen, bovine viral diarrhea glycoprotein 55, Newcastle disease virus hemagglutinin-neuraminidase, swine flu hemagglutinin, swine flu neuraminidase, foot and mouth disease virus, hog cholera virus, swine influenza virus, African swine fever virus, *Mycoplasma hyopneumoniae*, infectious bovine rhinotracheitis virus (e.g., infectious bovine rhinotracheitis virus glycoprotein E or glycoprotein G), or infectious laryngotracheitis virus (e.g., infectious laryngotracheitis virus glycoprotein G or glycoprotein I), a glycoprotein of La Crosse virus (Gonzales-Scarano et al., 1982, *Virology* 120: 42), neonatal calf diarrhea virus (Matsuno and Inouye, 1983, *Infection and Immunity* 39: 155), Venezuelan equine encephalomyelitis virus (Mathews and Roehrig, 1982, *J. Immunol.* 129: 2763), punta toro virus (Dalrymple et al., 1981, in Replication of Negative Strand Viruses, Bishop and Compans (eds.), Elsevier, NY, p. 167), murine leukemia virus (Steeves et al., 1974, *J. Virol.* 14:187), mouse mammary tumor virus (Massey and Schochetman, 1981, *Virology* 115: 20), hepatitis B virus core protein and/or hepatitis B virus surface antigen or a fragment or derivative thereof (see, e.g., U.K. Patent Publication No. GB 2034323A published Jun. 4, 1980; Ganem and Varmus, 1987, *Ann. Rev. Biochem.* 56:651-693; Tiollais et al., 1985, *Nature* 317:489-495), antigen of equine influenza virus or equine herpesvirus (e.g., equine influenza virus type A/Alaska 91 neuraminidase, equine influenza virus type A/Miami 63 neuraminidase, equine influenza virus type A/Kentucky 81 neuraminidase equine herpesvirus type 1 glycoprotein B, and equine herpesvirus type 1 glycoprotein D, antigen of bovine respiratory syncytial virus or bovine parainfluenza virus (e.g., bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase), bovine viral diarrhea virus glycoprotein 48 or glycoprotein 53.

Immunogens used in methods of this invention may also be a cancer antigen or a tumor antigen. Any cancer or tumor antigen known to one skilled in the art may be used in accordance with the immunogenic compositions of the invention including, but not limited to, KS ¼ pan-carcinoma antigen (Perez and Walker, 1990, *J. Immunol.* 142: 3662-3667; Bumal, 1988, *Hybridoma* 7(4): 407-415), ovarian carcinoma antigen (CA125) (Yu et al., 1991, *Cancer Res.* 51(2): 468-475), prostatic acid phosphate (Tailor et al., 1990, *Nucl. Acids Res.* 18(16): 4928), prostate specific antigen (Henttu and Vihko, 1989, *Biochem. Biophys. Res. Comm.* 160(2): 903-910; Israeli et al., 1993, *Cancer Res.* 53: 227-230), melanoma-associated antigen p97 (Estin et al., 1989, *J. Natl. Cancer Instit.* 81(6): 445-446), melanoma antigen gp75 (Vijayasardahl et al., 1990, *J. Exp. Med.* 171(4): 1375-1380), high molecular weight melanoma antigen (HMW-MAA) (Natali et al., 1987, *Cancer* 59: 55-63; Mittelman et al., 1990, *J. Clin. Invest.* 86: 2136-2144), prostate specific membrane antigen, carcinoembryonic antigen (CEA) (Foon et al., 1994, *Proc. Am. Soc. Clin. Oncol.* 13: 294), polymorphic epithelial mucin antigen, human milk fat globule antigen, colorectal tumor-associated antigens such as: CEA, TAG-72 (Yokata et al., 1992, *Cancer Res.* 52: 3402-3408), CO17-1A (Ragnhammar et al., 1993, *Int. J. Cancer* 53: 751-758); GICA 19-9 (Herlyn et al., 1982, *J. Clin. Immunol.* 2: 135), CTA-1 and LEA, Burkitt's lymphoma antigen-38.13, CD19 (Ghetie et al., 1994, *Blood* 83: 1329-1336), human B-lymphoma antigen-CD20 (Reff et al., 1994, *Blood* 83: 435-445), CD33 (Sgouros et al., 1993, *J Nucl. Med.* 34: 422-430), melanoma specific antigens such as ganglioside GD2 (Saleh et al., 1993, *J. Immunol.*, 151, 3390-3398), ganglioside GD3 (Shitara et al., 1993, *Cancer Immunol. Immunother.* 36: 373-380), ganglioside GM2 (Livingston et al., 1994, *J. Clin. Oncol.* 12:1036-1044), ganglioside GM3 (Hoon et al., 1993, *Cancer Res.* 53: 5244-5250), tumor-specific transplantation type of cell-surface antigen (TSTA) such as virally-induced tumor antigens including T-antigen DNA tumor viruses and Envelope antigens of RNA tumor viruses, oncofetal antigen-alpha-fetoprotein such as CEA of colon, bladder tumor oncofetal antigen (Hellstrom et al., 1985, *Cancer. Res.* 45: 2210-2188), differentiation antigen such as human lung carcinoma antigen L6, L20 (Hellstrom et al., 1986, *Cancer Res.* 46: 3917-3923), antigens of fibrosarcoma, human leukemia T cell antigen-Gp37 (Bhattacharya-Chatterjee et al., 1988, *J. of Immunospecifically.* 141: 1398-1403), neoglycoprotein, sphingolipids, breast cancer antigen such as EGFR (Epidermal growth factor receptor), HER2 antigen ($p85^{HER2}$), polymorphic epithelial mucin (PEM) (Hilkens et al., 1992, *Trends in Bio. Chem. Sci.* 17: 359), malignant human lymphocyte antigen-APO-1 (Bernhard et al., 1989, *Science* 245: 301-304), differentiation antigen (Feizi, 1985, *Nature* 314: 53-57) such as I antigen found in fetal erythrocytes, primary endoderm, I antigen found in adult erythrocytes, preimplantation embryos, I (Ma) found in gastric adenocarcinomas, M18, M39 found in breast epithelium, SSEA-1 found in myeloid cells, VEP8, VEP9, Myl, VIM-D5, $D_1$56-22 found in colorectal cancer, TRA-1-85 (blood group H), C14 found in colonic adenocarcinoma, F3 found in lung adenocarcinoma, AH6 found in gastric cancer, Y hapten, Le$^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma antigen, CO-514 (blood group Le$^a$) found in Adenocarcinoma, NS-10 found in adenocarcinomas, CO-43 (blood group Le$^b$), G49 found in EGF receptor of A431 cells, MH2 (blood group ALe$^b$/Le$^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, and M1:22:25:8 found in embryonal carcinoma cells, and SSEA-3 and SSEA-4 found in 4 to 8-cell stage embryos. In one embodiment, the antigen is a T cell receptor derived peptide from a Cutaneous T cell Lymphoma (see, Edelson, 1998, *The Cancer Journal* 4: 62).

In a preferred embodiment, the immunogenic composition used in methods of this invention is a cancer vaccine. Examples of cancer vaccines include, but are not limited to: antigen modified denritic cell (DC) vaccines such as, but not limited to, Provenge, Neuvenge, Immunovex, Telomerase vaccine, Uvidem, Collidem, DCVax-prostate, and DCVax-brain; peptide vaccines such as, but not limited to, Theratope, L-BLP25, Oncophage (HSPPC-96), GTOPO-99, IGN-101, FavId, Panvac-VF, Prostvac-VF, Avicine, EP-2101, MyVax, Biovaxid, Mitumomab (IMC-BEC2), IMG-GP75, HER-2 DNA/Protein AutoVac, Zyc 300, and HER-2 protein AutoVac; whole tumor cell vaccines such as, but not limited to, Canvaxin, Ony-P, Melacine, GVAX, GVAX and MDX-010, and Oncovax; and viral vector vaccines such as, but not limited to, ALVAC-CEA/B&1, Allovectin-7, ALVAC, Lovaxin C, AdhTAP(OS-1), TroVax, and MVA-MUC1-IL2 (TG4010). Characteristics of these vaccines are summarized in Tables 1-4.

Immunogens may comprise a virus, against which an immune response is desired. In certain cases, the immunogenic composition used in methods of this invention comprise recombinant or chimeric viruses. In other cases, the immunogenic composition comprises a virus which is attenuated. Production of recombinant, chimeric and attenuated viruses may be performed using standard methods known to one skilled in the art. This invention also encompasses a live recombinant viral vaccine or an inactivated recombinant viral vaccine to be formulated in accordance with the invention. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

Recombinant virus may be non-pathogenic to the subject to which it is administered. In this regard, the use of genetically engineered viruses for vaccine purposes may require the presence of attenuation characteristics in these strains. The introduction of appropriate mutations (e.g., deletions) into the templates used for transfection may provide the novel viruses with attenuation characteristics. For example, specific missense mutations which are associated with temperature sensitivity or cold adaptation can be made into deletion mutations. These mutations should be more stable than the point mutations associated with cold or temperature sensitive mutants and reversion frequencies should be extremely low.

Alternatively, chimeric viruses with "suicide" characteristics may be constructed for use in the immunogenic compositions. Such viruses would go through only one or a few rounds of replication within the host. When used as a vaccine, the recombinant virus would go through limited replication cycle(s) and induce a sufficient level of immune response but it would not go further in the human host and cause disease.

Alternatively, inactivated (killed) virus may be formulated in accordance with the invention. Inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled.

Completely foreign epitopes, including antigens derived from other viral or non-viral pathogens can also be engineered into the virus for use in immunogenic compositions. For example, antigens of non-related viruses such as HIV (gp160, gp120, gp41) parasite antigens (e.g., malaria), bacterial or fungal antigens or tumor antigens can be engineered into the attenuated strain. Typically such methods include inoculating embryonated eggs, harvesting the allantoic fluid, concentrating, purifying and separating the whole virus, using for example zonal centrifugation, ultracentrifugation, ultrafiltration, and chromatography in a variety of combinations.

Virtually any heterologous gene sequence may be constructed into the chimeric viruses for use in immunogenic compositions. Preferably, heterologous gene sequences are moieties and peptides that act as biological response modifiers. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses include, but are not limited to, influenza and parainfluenza hemagglutinin neuraminidase and fusion glycoproteins such as the HN and F genes of human PIV3. In addition, heterologous gene sequences that can be engineered into the chimeric viruses include those that encode proteins with immuno-modulating activities. Examples of immuno-modulating proteins include, but are not limited to, cytokines, interferon type 1, gamma interferon, colony stimulating factors, interleukin-1, -2, -4, -5, -6, -12, and antagonists of these agents.

Other heterologous sequences may be derived from tumor antigens, and the resulting chimeric viruses be used to generate an immune response against the tumor cells leading to tumor regression in vivo. In accordance with the present invention, recombinant viruses may be engineered to express tumor-associated antigens (TAAs), including but not limited to, human tumor antigens recognized by T cells (Robbins and Kawakami, 1996, *Curr. Opin. Immunol.* 8:628-636, incorporated herein by reference in its entirety); melanocyte lineage proteins, including gp100, MART-1/MelanA, TRP-1 (gp75) and tyrosinase; tumor-specific widely shared antigens, such as MAGE-1, MAGE-3, BAGE, GAGE-1, GAGE-1, N-acetylglucosaminyltransferase-V and p15; tumor-specific mutated antigens, such as β-catenin, MUM-1 and CDK4; non-melanoma antigens for breast, ovarian, cervical and pancreatic carcinoma, HER-2/neu, human papillomavirus-E6, -E7, MUC-1.

5.1.2 Vaccines and Target Diseases

A wide variety of vaccines may be used in connection with methods of this invention. A non-limiting list of vaccines that can be used in connection with this invention is provided in FIG. 1. Target diseases for methods of the invention includes cancer, other infectious or inflammatory diseases.

Methods of the invention can be used in the treatment of cancers, including, but not limited to, neoplasms, tumors, metastases, or any disease or disorder characterized by uncontrolled cell growth. Specific examples of cancer include, but are not limited to: cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. Methods of the invention are particularly useful for treating cancers of the blood and bone marrow, such as multiple myeloma and acute and chronic leukemias, for example, lymphoblastic, myelogenous, lymphocytic, myelocytic leukemias, and myelodysplastic syndromes including but not limited to 5 q minus syndrome, or myelodysplastic syndromes associated with other cytogenic abnormalities. The methods of the invention can be used for treating, preventing or managing either primary or metastatic tumors.

Other specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scelroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation.

Infectious diseases are caused by infectious agents such as, but not limited to, viruses, bacteria, fungi protozoa, helminths, and parasites.

Examples of viruses that have been found in humans include, but are not limited to, Retroviridae (e.g., human immunodeficiency viruses, such as HIV-1 (also referred to as HTLV-III, LAV or HTLV-III/LAV, or HIV-III; and other isolates, such as HIV-LP); Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (e.g., hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted, e.g., Hepatitis C); Norwalk and related viruses, and astroviruses.

Retroviruses that results in infectious diseases in animals and humans include both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of RNA viruses that are antigenic or immunogenic in vertebrate animals include, but are not limited to, the following: members of the family Reoviridae, including the genus *Orthoreovirus* (multiple serotypes of both mammalian and avian retroviruses), the genus *Orbivirus* (Bluetongue virus, Eugenangee virus, Kemerovo virus, African horse sickness virus, and Colorado Tick Fever virus), the genus *Rotavirus* (human rotavirus, Nebraska calf diarrhea virus, murine rotavirus, simian rotavirus, bovine or ovine rotavirus, avian rotavirus); the family Picornaviridae, including the genus *Enterovirus* (poliovirus, Coxsackie virus A and B, enteric cytopathic human orphan (ECHO) viruses, hepatitis A virus, Simian enteroviruses, Murine encephalomyelitis (ME) viruses, *Poliovirus muris*, Bovine enteroviruses, Porcine enteroviruses), the genus *Cardiovirus* (Encephalomyocarditis virus (EMC), Mengovirus), the genus *Rhinovirus* (Human rhinoviruses including at least 113 subtypes; other rhinoviruses), the genus *Apthovirus* (Foot and Mouth disease (FMDV); the family Calciviridae, including Vesicular exanthema of swine virus, San Miguel sea lion virus, Feline picornavirus and Norwalk virus; the family Togaviridae, including the genus *Alphavirus* (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza* virus (Influenza virus type A (many human subtypes), Swine influenza virus, and Avian and Equine Influenza viruses, influenza type B (many human subtypes), and influenza type C (possible separate genus)); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza* virus (Influenza virus type A, many human subtypes); Swine influenza virus, and Avian and Equine Influenza viruses; influenza type B (many human subtypes), and influenza type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); the family Rhabdoviridae, including the genus *Vesiculovirus* (VSV), Chandipura virus, Flanders-Hart Park virus), the genus *Lyssavirus* (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that are antigenic or immunogenic in vertebrate animals include, but are not limited to: the family Poxyiridae, including the genus *Orthopoxvirus* (Variola major, Variola minor, Monkey pox Vaccinia, Cowpox, Buffalopox, Rabbitpox, Ectromelia), the genus *Leporipoxvirus* (Myxoma, Fibroma), the genus *Avipoxvirus* (Fowlpox, other avian poxvirus), the genus *Capripoxvirus* (sheeppox, goatpox), the genus *Suipoxvirus* (Swinepox), the genus *Parapoxvirus* (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus), the Beta-herpesviruses (Human cytomegalovirus and cytomegaloviruses of swine, monkeys and rodents), the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus *Mastadenovirus* (Human subgroups A, B, C, D, E and ungrouped; simian adenoviruses (at least 23 serotypes), infectious canine hepatitis, and adenoviruses of cattle, pigs, sheep, frogs and many other species), the genus *Aviadenovirus* (Avian adenoviruses), and non-cultivatable adenoviruses; the family Papoviridae, including the genus *Papillomavirus* (Human papilloma viruses, bovine papilloma viruses, Shope rabbit papilloma virus, and various pathogenic papilloma viruses of other species), the genus *Polyomavirus* (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus *Parvovirus* (Feline panleukopenia virus, bovine parvovirus, canine parvovirus, Aleutian mink disease virus, etc). Finally, DNA viruses may include viruses which do not fit into the above families such as Kuru and Creutzfeldt-Jacob disease viruses and chronic infectious neuropathic agents.

Bacterial infections or diseases that can be treated by methods of the present invention are caused by bacteria including, but not limited to, bacteria that have an intracellular stage in its life cycle, such as mycobacteria (e.g., *Mycobacteria tuberculosis, M. bovis, M. avium, M. leprae*, or *M. africanum*), rickettsia, mycoplasma, chlamydia, and legionella. Other examples of bacterial infections contemplated include, but are not limited to, infections caused by Gram positive *bacillus* (e.g., *Listeria, Bacillus* such as *Bacillus anthracis, Erysipelothrix* species), Gram negative *bacillus* (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio*, and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, *Neisseria* species. Specific examples of infectious bacteria include, but are not limited to: *Helicobacter pyloris, Borelia burgdorferi, Legionella pneumophilia, Mycobacteria tuberculosis, M. avium, M. intracellulare, M. kansaii, M. gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, corynebacterium diphtheriae, Erysipelothrix rhusiopathiae, Clostridium perfringers, Clostridium tetani, Enterobacter aerogenes, Klebsiella pneumoniae, Pasturella multocida, Fusobacterium nucleatum, Streptobacillus moniliformis, Treponema pallidium, Treponema pertenue, Leptospira, Rickettsia, and Actinomyces israelli.

Fungal diseases that can be treated by methods of the present invention include, but are not limited to, aspergilliosis, crytococcosis, sporotrichosis, coccidioidomycosis, paracoccidioidomycosis, histoplasmosis, blastomycosis, zygomycosis, and candidiasis.

Parasitic diseases that can be treated by methods of the present invention include, but are not limited to, amebiasis, malaria, leishmania, coccidia, giardiasis, cryptosporidiosis, toxoplasmosis, and trypanosomiasis. Also encompassed are infections by various worms such as, but not limited to, ascariasis, ancylostomiasis, trichuriasis, strongyloidiasis, toxoccariasis, trichinosis, onchocerciasis, filaria, and dirofilariasis. Also encompassed are infections by various flukes such as, but not limited to, schistosomiasis, paragonimiasis, and clonorchiasis. Parasites that cause these diseases can be classified based on whether they are intracellular or extracellular. An "intracellular parasite," as used herein, is a parasite whose entire life cycle is intracellular. Examples of human intracellular parasites include *Leishmania* spp., *Plasmodium* spp., *Trypanosoma cruzi, Toxoplasma gondii, Babesia* spp., and *Trichinella spiralis*. An "extracellular parasite," as used herein, is a parasite whose entire life cycle is extracellular. Extracellular parasites capable of infecting humans include *Entamoeba histolytica, Giardia lamblia, Enterocytozoon bieneusi, Naegleria* and *Acanthamoeba* as well as most helminths. Yet another class of parasites is defined as being mainly extracellular but with an obligate intracellular existence at a critical stage in their life cycles. Such parasites are referred to herein as "obligate intracellular parasites." These parasites may exist most of their lives or only a small portion of their lives in an extracellular environment, but they all have at least one obligate intracellular stage in their life cycles. This latter category of parasites includes *Trypanosoma rhodesiense* and *Trypanosoma gambiense, Isospora* spp., *Cryptosporidium* spp, *Eimeria* spp., *Neospora* spp., *Sarcocystis* spp., and *Schistosoma* spp.

5.2 Allergens

This invention encompasses methods of reducing or inhibiting allergic reaction to an allergen in a subject comprising administering to the subject an immunomodulatory compound of the invention prior to the subject's exposure to an allergen. Optionally, in addition to the administration before the exposure to an allergen, an immunomodulatory compound may be administered during and/or after the subject's exposure to an allergen. It is contemplated that any types of exposure to allergens including, but not limited to, the subject's exposure to naturally occurring allergens, exposure by the intake of food, and exposure through allergy vaccine administration, are encompassed by methods of this invention.

Examples of allergens (e.g., naturally occurring or those contained in allergy vaccines) include, but are not limited to, allergens from:

mites such as, but not limited to, *Dermatophagoides farinae, Dermatophagoides pteronyssinus, Acarus siro, Blomia tropicalis, Chortoglyphus arcuatas, Euroglyphus maynei, Lepidoglyphus destructor, Tyrophagus putrescentiae*, and *Glyphagus demesticus*;

venoms such as, but not limited to, *Bombus* spp., *Vespa crabro, Apis mellifera, Dolichovespula* spp., *Polistes* spp., *Vespula* spp., *Dolichovespula maculata*, and *Dolichovespula arenaria*;

insects such as, but not limited to, *Camponotus pennsylvanicus, Solenopsis invicta, Solenopsis richteri, Periplaneta americana, Blattella germanica, Blatta orientails, Tebanus* spp., *Musca domestica, Ephemeroptera* spp., *Culicidae* sp., and *Heterocera* spp.;

epithelia, dander, hair and features such as, but not limited to, *Serinus canaria, Felis catus (domesticus), Bos taurus, Gallus gallus (domesticus), Canis familiaris, Anas platyrhynchos, Meriones unguiculatus, Capra hircus, Anser domesticus, Cavia porcellus (cobaya), Mesocrietus auratus, Sus scrofa, Equus caballus, Mus musculus, Psittacidae, Columbafasciata, Oryctolagus cuniculus, Rattus norvegicus*, and *Ovis aries*;

fungi such as, but not limited to, *Cephalosporium acremonium, Alternaria tenuis, Aspergillus glaucus, Aspergillus flavus, Aspergillus fumigatus, Aspergillus nidulans, Aspergillus niger, Aspergillus terreus, Aspergillus versicolor, Aureobasidium pullulan (Pullularia pullulans), Drechslera sorokiniana, Helminthosporium sativum, Botrytis cinerea, Candida albicans, Chaetomium globosum, Cladosporium herbarum, Cladosporium sphaerospermum(Homodendrum hordei), Drechslera spicifera (Curvularia spicifera), Epicoccum nigrum (Epicoccum purpurascens), Epidermophyton floccosum, Fusarium moniliforme, Fusarium solani, Geotrichum candidum, Gliocladium viride, Helminthosporium solani, Microsporum canis, Mucor circinelloides f. circinelloides, Mucor circinelloidesf lusitanicus, Mucor plumbeus, Mycogone perniciosa, Neurospora intermedia, Nigrospora oryzae, Paecilomyces variotii, Penicillum brevi-compactum, Penicillum camembertii, Penicillum chrysogenum, Penicillum digitatum, Penicillum expansum, Penicillum notatum, Penicillum roquefortii, Phoma betae, Phoma herbarum, Rhizopus oryzae, Rhizopus stolonifer, Rhodotorula mucilaginosa, Saccharomyces cerevisiae, Scopulariopsis brevicaulis, Serpula lacrymans, Setosphaeria rostrata, Stemphylium botryosum, Stemphylium solani, Trichoderma harzianum, Trichophyton mentagrophytes, Trichophyton rubrum*, and *Trichothecium roseum*;

smuts such as, but not limited to, *Ustilago nuda, Ustilago cynodontis, Ustilago maydis, Sporisorium cruentum, Ustilago avenae*, and *Ustilago tritici*;

grasses such as, but not limited to, *Paspalum notatum, Cynodon dactylon, Poa compressa, Bromus inermis, Phalaris arundinacea, Zea mays, Elytrigia repens (Agropyron repens), Sorghum haelpense, Poa pratensis, Festuca pratensis (elatior), Avena sativa, Dactylis glomerata, Agrostis gigantea (alba), Secale cereale, Leymus (Elymus) condensatus, Lolium perenne* ssp. *multiflorum, Lolium perenne, Anthoxanthum odoratum, Phleum pratense, Holcus lanatus, Triticum aestivum*, and *Elymus (Agropyron) smithii*;

weeds such as, but not limited to, *Atriplex polycarpa, Baccharis halimifolia, Baccharis sarothroides, Hymenoclea salsola, Amaranthus hybridus, Xanthium strumarium (commune), Rumex crispus, Eupathium capillifolium, Solidago* spp., *Amaranthus tuberculatus (Acnida tamariscina), Allenrolfea occidentalis, Chenopodium botrys, Kochia scoparia, Chenopodium album, Iva xanthifolia, Iva angustifolia, Chenopodium ambrosioides, Artemisia vulgaris, Artemisia ludoviciana, Urtica dioica, Amaranthus spinosus, Plantago lanceolata, Iva axillaris, Atriplex lentiformis, Ambrosia dumosa, Ambrosia acanthicarpa, Ambrosia trifida, Ambrosia artemisiifolia, Ambrosia confertiflora, Ambrosia bidentata, Ambrosia psilostachya, Salsola kali (pestifer), Artemisia californica, Artemisiafrigida, Artemisia tridentata, Atriplex wrightii, Atriplex confertifolia*, and *Artemisia annua*;

trees such as, but not limited to, *Acasia* spp., *Alnus glutinosa, Alnus rubra, Alnus incana* ssp. *rugosa, Alnus rhombifolia, Fraxinus velutina, Fraxinus pennsylvanica, Fraxinus latifolia, Fraxinus americana, Populus tremuloides, Myrica* cerifera, Fagus grandifolia (americana), Casuarina equisetifolia, Betula lenta, Betula pendula, Betula nigra, Betula occidentalis (fontinalis), Betula populifolia, Acer negundo, Cryptomeria japonica, Juniperus ashei (sabinoides), Juniperus virginiana, Tamarix gallica, Populus balsamifera ssp. trichocarpa, Populus deltoides, Populusfremontii, Populus wislizeni, Populus monilifera (sargentii), Cupressus arizonoca, Taxodium distichum, Cupressus sempervirens, Ulmus americana, Ulmus crassifolia, Ulmus pumila, Eucalyptus globulus, Celtis occidentalis, Corylus americana, Corylus avellana, Carya ovata, Carya laciniosa, Carya alba, Juniferus monosperma, Juniperus princhotii, Juniperus scopulorum, Juniperus occidentalis, Robinia pseudoacacia, Mangifera indica, Acer macrophyllum, Acer rubrum, Acer saccharum, Melaleuca quinquenervia (leucadendron), Prosopis glandulosa (juliflora), Broussonetia papyrifera, Morus rubra, Morus alba, Quercus gambelii, Quercus velutina, Quercus macrocarpa, Quercus kelloggii, Quercus agrifolia, Quercus lobata, Quercus ilex, Quercus stellata, Quercus rubra, Quercus dumosa, Quercus virginiana, Quercus nigra, Quercus garryana, Quercus alba, Olea europaea, Elaegnus angustifolia, Citrus sinensis, Arecastrum romanzoffianum (Cocos plumosa), Carya illnoensis, Schinus molle, Schinus terebinthifolius, Pinus taeda, Pinus strobus, Pinus palustris, Pinus ponderosa, Pinus elliottii, Pinus virginiana, Pinus monticola, Pinus echinata, Populus nigra, Populus alba, Ligustrum vulgare, Liquidambar styraciflua, Platanus occidentalis, Platanus orientalis, Platanus racemosa, Platanus acerifolia, Juglans nigra, Juglans californica, Juglans regia, Salix lasiolepsis, Salix nigra, and Salix discolor;

flowers such as, but not limited to, *Chrysanthemum leucanthemum*, *Taraxacum officinale*, and *Helianthus annuus*;

farm plants such as, but not limited to, *Medicago sativa*, *Ricinus communis*, *Trifolium pratense*, *Brassica* spp., and *Beta vulgaris*;

plant food such as, but not limited to, Prunus dulcis, Maluspumila, Prunus armeniaca, Musa paradisiaca (sapientum), Hordeum vulgare, Phaseolus lunatus, Phaseolus vulgaris, Phaseolus sp., Phaseolus sp., Phaseolus vulgaris, Rubus allegheniensis, Vaccinium sp., Brassica oleracea var. botrytis, Fagopyrum esculentum, Brassica oleracea var. capitata, Theobroma cacao, Cucumis melo, Daucus carota, Brassica oleracea var. botrytis, Apium graveolens var. dulce, Prunus sp., Cinnamomum verum, Coffea arabic, Zea mays, Vaccinium macrocarpon, Cucumis sativus, Allium sativum, Zingiber officinale, Vitis sp., Citrus paradisi, Humulus lupulus, Citrus limon, Lactuca sativa, Agaricus campestris, Brassica sp., Myristica fragrans, Avena sativa, Olea europaea, Allium cepa var. cepa, Citrus sinensis, Vigna unguiculata, Pisum sativum, Prunus persica, Pyrus communis, Piper nigrum, Capsicum annuum var. annuum, Ananas comosus, Ipomoea batatas, Solanum tuberosum, Rubus idaeus var. idaeus, Oryza sativa, Secale cereale, Sesamum orientale (indicum), Glycine max, Spinacia oleracea, Cucurbita pepo var. melopepo, Fragaria chiloensis, Lycopersicon esculentum (lycopersicum), Brassica rapa var. rapa, Vanilla planifolia, Citrullus lanatus var. lanatus, and Triticun aestivum;

fish and shellfish such as, but not limited to, *Micropterus* sp., *Ictalurus punctatus*, *Mercenaria mercenaria*, *Gadus morhua*, *Callinectes sapidus*, *Platichthys* sp., *Hippoglossus* sp., *Homarus americanus*, *Scomber scombrus*, *Crassostrea virginica*, *Sebastes marinus*, *Salmo salar*, *Clupeiformes*, *Pecten magellanicus*, *Penaeus* sp., *Salvelinus* sp., and *Thunnus* sp.;

animal foods such as, but not limited to, *Bos taurus*, *Ovis aries*, and *Sus scrofa*;

poultry products such as, but not limited to, chicken (*Gallus gallus*) products and turkey (*Meleagris gallopavo*) products;

dairy products such as, but not limited to, bovine casein and bovine milk;

nuts such as, but not limited to, *Bertholletia excelsa*, *Anacardium occidentale*, *Cocos nucifera*, *Corylus americana*, *Arachis hypogaea*, *Carya illinoensis*, *Juglans nigra*, and *Juglans regia*;

miscellaneous allergens such as, but not limited to, those from *Gossypium hirsutum*, *Linum usitatissimum*, *Acaia senegal*, *Sterculia urens*, *Astragalus gummifer*, *Ceiba pentandra*, *Iris germanica* var. *florentina*, *Chrysanthemum cinerariifolium*, *Bombyx mori*, and *Nicotiana tabacum*;

dust such as, but not limited to, barley grain dust, corn grain dust, house dust, mattress dust, oat grain dust, wheat grain dust, and upholstery dust.

5.3 Immunomodulatory Compounds

As used herein and unless otherwise indicated, the terms "immunomodulatory compounds of the invention" and "IMiDs®" (Celgene Corporation) encompass certain small organic molecules that inhibit LPS induced monocyte TNF-α, IL-1β, IL-12, IL-6, MIP-1α, MCP-1, GM-CSF, G-CSF, and COX-2 production. Specific immunomodulatory compounds are discussed below.

TNF-α is an inflammatory cytokine produced by macrophages and monocytes during acute inflammation. TNF-α is responsible for a diverse range of signaling events within cells. Without being limited by a particular theory, one of the biological effects exerted by the immunomodulatory compounds of the invention is the reduction of myeloid cell TNF-α production. Immunomodulatory compounds of the invention may enhance the degradation of TNF-α mRNA.

Further, without being limited by theory, immunomodulatory compounds used in the invention may also be potent co-stimulators of T cells and increase cell proliferation dramatically in a dose dependent manner. Immunomodulatory compounds of the invention may also have a greater co-stimulatory effect on the CD8+ T cell subset than on the CD4+ T cell subset. In addition, the compounds preferably have anti-inflammatory properties against myeloid cell responses, yet efficiently co-stimulate T cells to produce greater amounts of IL-2, IFN-γ, and to enhance T cell proliferation and CD8+ T cell cytotoxic activity. Further, without being limited by a particular theory, immunomodulatory compounds used in the invention may be capable of acting both indirectly through cytokine activation and directly on Natural Killer ("NK") cells and Natural Killer T ("NKT") cells, and increase the NK cells' ability to produce beneficial cytokines such as, but not limited to, IFN-γ, and to enhance NK and NKT cell cytotoxic activity.

Specific examples of immunomodulatory compounds include cyano and carboxy derivatives of substituted styrenes such as those disclosed in U.S. Pat. No. 5,929,117; 1-oxo-2-(2,6-dioxo-3-fluoropiperidin-3-yl)isoindolines and 1,3-dioxo-2-(2,6-dioxo-3-fluoropiperidine-3-yl)isoindolines such as those described in U.S. Pat. Nos. 5,874,448 and 5,955,476; the tetra substituted 2-(2,6-dioxopiperdin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide), substituted 2-(2,6-dioxopiperidin-3-yl)phthalimides and substituted 2-(2,6- dioxopiperidin-3-yl)-1-oxoisoindoles including, but not limited to, those disclosed in U.S. Pat. Nos. 5,635,517, 6,281,230, 6,316,471, 6,403,613, 6,476,052 and 6,555,554; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; and isoindole-imide compounds such as those described in U.S. patent publication no. 2003/0045552 published on Mar. 6, 2003, U.S. patent publication no. 2003/0096841 published on May 22, 2003, and International Application No. PCT/US01/50401 (International Publication No. WO 02/059106). The entireties of each of the patents and patent applications identified herein are incorporated herein by reference. Immunomodulatory compounds do not include thalidomide.

Various immunomodulatory compounds of the invention contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular immunomodulatory compounds of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

Preferred immunomodulatory compounds of the invention include, but are not limited to, 1-oxo- and 1,3dioxo-2-(2,6-dioxopiperidin-3-yl)isoindolines substituted with amino in the benzo ring as described in U.S. Pat. No. 5,635,517 which is incorporated herein by reference. These compounds have the structure I:

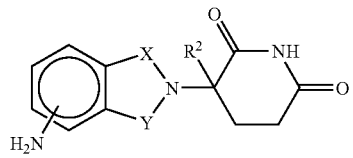

in which one of X and Y is C=O, the other of X and Y is C=O or CH$_2$, and R$^2$ is hydrogen or lower alkyl, in particular methyl. Specific immunomodulatory compounds include, but are not limited to:

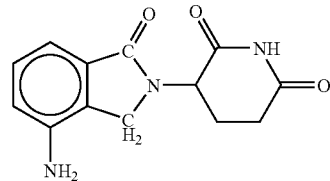

1-oxo-2-(2,6-dioxopiperidin-3-yl)-4-aminoisoindoline;

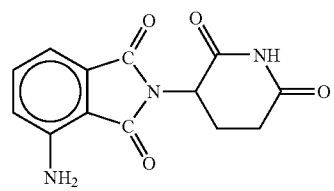

1,3-dioxo-2-(2,6-dioxopiperidin-3-yl)-4-aminoisoindoline; and

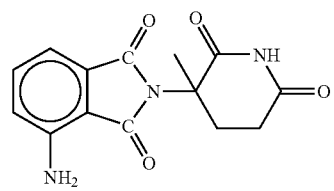

1,3-dioxo-2-(3-methyl-2,6-dioxopiperidin-3-yl)-4-aminoisoindole, and optically pure isomers thereof. The compounds can be obtained via standard, synthetic methods (see e.g., U.S. Pat. No. 5,635,517, incorporated herein by reference). The compounds are also available from Celgene Corporation, Warren, N.J.

As used herein, and unless otherwise indicated, the term "optically pure" means a composition that comprises one optical isomer of a compound and is substantially free of other isomers of that compound. For example, an optically pure composition of a compound having one chiral center will be substantially free of the opposite enantiomer of the compound. An optically pure composition of a compound having two chiral centers will be substantially free of other diastereomers of the compound. A typical optically pure compound comprises greater than about 80% by weight of one enantiomer of the compound and less than about 20% by weight of other enantiomers of the compound, more preferably greater than about 90% by weight of one enantiomer of the compound and less than about 10% by weight of the other enantiomers of the compound, even more preferably greater than about 95% by weight of one enantiomer of the compound and less than about 5% by weight of the other enantiomers of the compound, more preferably greater than about 97% by weight of one enantiomer of the compound and less than about 3% by weight of the other enantiomers of the compound, and most preferably greater than about 99% by weight of one enantiomer of the compound and less than about 1% by weight of the other enantiomers of the compound.

Other specific immunomodulatory compounds of the invention belong to a class of substituted 2-(2,6-dioxopiperidin-3-yl)phthalimides and substituted 2-(2,6-dioxopiperidin-3-yl)-1-oxoisoindoles, such as those described in U.S. Pat.

Nos. 6,281,230; 6,316,471; 6,335,349; and 6,476,052, and International Patent Application No. PCT/US97/13375 (International Publication No. WO 98/03502), each of which is incorporated herein by reference. Representative compounds are of formula:

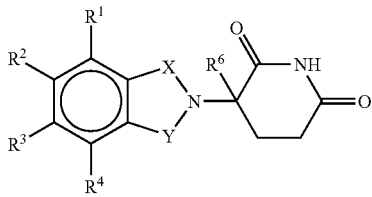

in which:

one of X and Y is C=O and the other of X and Y is C=O or $CH_2$;

(i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;

$R^5$ is hydrogen or alkyl of 1 to 8 carbon atoms;

$R^6$ is hydrogen, alkyl of 1 to 8 carbon atoms, benzyl, or halo;

provided that $R^6$ is other than hydrogen if X and Y are C=O and (i) each of $R^1$, $R^2$, $R^3$, and $R^4$ is fluoro or (ii) one of $R^1$, $R^2$, $R^3$, or $R^4$ is amino.

Compounds representative of this class are of the formulas:

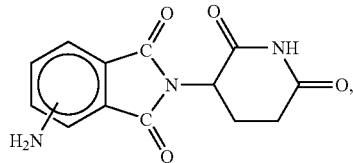

and

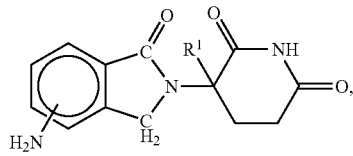

wherein $R^1$ is hydrogen or methyl. In a separate embodiment, the invention encompasses the use of enantiomerically pure forms (e.g. optically pure (R) or (S) enantiomers) of these compounds.

Still other specific immunomodulatory compounds of the invention belong to a class of isoindole-imides disclosed in U.S. Patent Application Publication Nos. US 2003/0096841 and US 2003/0045552, and International Application No. PCT/US01/50401 (International Publication No. WO 02/059106), each of which are incorporated herein by reference. Representative compounds are of formula II:

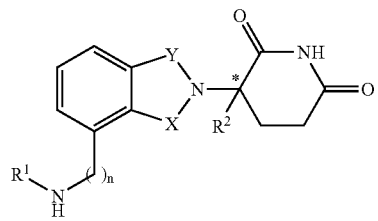

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(S)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(O)NHR^3$, $C(S)NHR^3$, $C(O)NR^3R^{3'}$, $C(S)NR^3R^{3'}$ or $(C_1-C_8)$alkyl-$O(CO)R^5$;

$R^2$ is H, F, benzyl, $(C_1-C_8)$alkyl, $(C_2-C_8)$alkenyl, or $(C_2-C_8)$alkynyl;

$R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;

$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$(C_1-C_6)$heterocycloalkyl, or $(C_0-C_4)$alkyl-$OC_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-$C(O)O$—$R^5$ or the $R^6$ groups can join to form a heterocycloalkyl group;

n is 0 or 1; and

* represents a chiral-carbon center.

In specific compounds of formula II, when n is 0 then $R^1$ is $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(S)NHR^3$, or $(C_1-C_8)$alkyl-$O(CO)R^5$;

$R^2$ is H or $(C_1-C_8)$alkyl; and $R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_5-C_8)$alkyl-$N(R^6)_2$; $(C_0-C_8)$alkyl-NH—$C(O)OR^5$; $(C_1-C_8)$alkyl-$OR^5$, $(C_1-C_8)$alkyl-$C(O)OR^5$, $(C_1-C_8)$alkyl-$O(CO)R^5$, or $C(O)OR^5$; and the other variables have the same definitions.

In other specific compounds of formula II, $R^2$ is H or $(C_1-C_4)$alkyl.

In other specific compounds of formula II, $R^1$ is $(C_1-C_8)$alkyl or benzyl.

In other specific compounds of formula II, $R^1$ is H, $(C_1-C_8)$alkyl, benzyl, $CH_2OCH_3$, $CH_2CH_2OCH_3$, or

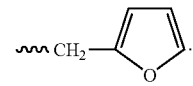

In another embodiment of the compounds of formula II, $R^1$ is wherein Q is O or S, and each occurrence of $R^7$ is independently H, $(C_1-C_8)$alkyl, $(C_3-C_7)$cycloalkyl, $(C_2-C_8)$alkenyl, $(C_2-C_8)$alkynyl, benzyl, aryl, halogen, $(C_0-C_4)$alkyl-$(C_1-C_6)$ heterocycloalkyl, $(C_0-C_4)$alkyl-$(C_2-C_5)$heteroaryl, $(C_0-C_8)$ alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$, or adjacent occurrences of $R^7$ can be taken together to form a bicyclic alkyl or aryl ring.

In other specific compounds of formula II, $R^1$ is $C(O)R^3$.

In other specific compounds of formula II, $R^3$ is (C0-C4) alkyl-C2-C5)heteroaryl, (C1-C8)alkyl, aryl, or $(C_0-C_4)$alkyl-$OR^5$.

In other specific compounds of formula II, heteroaryl is pyridyl, furyl, or thienyl.

In other specific compounds of formula II, $R^1$ is $C(O)OR^4$.

In other specific compounds of formula II, the H of C(O) NHC(O) can be replaced with $(C_1-C_4)$alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl)methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl) carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl] methyl}(octylamino)carboxamide; and N-{[2-(2,6-dioxo(3-piperidyl))-1,3-dioxoisoindolin-4-yl]methyl}(benzylamino) carboxamide.

Still other specific immunomodulatory compounds of the invention belong to a class of isoindole-imides disclosed in U.S. Patent Application Publication Nos. US 2002/0045643, International Publication No. WO 98/54170, and U.S. Pat. No. 6,395,754, each of which is incorporated herein by reference. Representative compounds are of formula III:

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

R is H or $CH_2OCOR'$;

(i) each of $R^1, R^2, R^3$, or $R^4$, independently of the others, is halo, alkyl of 1 to 4 carbon atoms, or alkoxy of 1 to 4 carbon atoms or (ii) one of $R^1, R^2, R^3$, or $R^4$ is nitro or —$NHR^5$ and the remaining of $R^1, R^2, R^3$, or $R^4$ are hydrogen;

$R^5$ is hydrogen or alkyl of 1 to 8 carbons $R^6$ hydrogen, alkyl of 1 to 8 carbon atoms, benzo, chloro, or fluoro;

R' is $R^7$—$CHR^{10}$—$N(R^8R^9)$;

$R^7$ is m-phenylene or p-phenylene or —$(C_nH_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X_1CH_2CH_2$— in which $X_1$ is —O—, —S—, or —NH—;

$R^{10}$ is hydrogen, alkyl of to 8 carbon atoms, or phenyl; and

* represents a chiral-carbon center.

Other representative compounds are of formula:

wherein:

one of X and Y is C=O and the other of X and Y is C=O or $CH_2$;

(i) each of $R^1, R^2, R^3$, or $R^4$, independently of the others, is halo, alkyl of 1 to 4 carbon atoms, or alkoxy of 1 to 4 carbon atoms or (ii) one of $R^1, R^2, R^3$, and $R^4$ is —$NHR^5$ and the remaining of $R^1, R^2, R^3$, and $R^4$ are hydrogen;

$R^5$ is hydrogen or alkyl of 1 to 8 carbon atoms;

$R^6$ is hydrogen, alkyl of 1 to 8 carbon atoms, benzo, chloro, or fluoro;

$R^7$ is m-phenylene or p-phenylene or —$(C_nH_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —CH$_2$CH$_2$X$^1$CH$_2$CH$_2$— in which X$^1$ is —O—, —S—, or —NH—; and R$^{10}$ is hydrogen, alkyl of to 8 carbon atoms, or phenyl.

Other representative compounds are of formula:

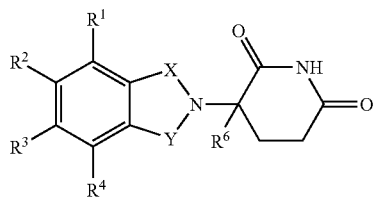

in which
one of X and Y is C═O and the other of X and Y is C═O or CH$_2$;
each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is nitro or protected amino and the remaining of R$^1$, R$^2$, R$^3$, and R$^4$ are hydrogen; and
R$^6$ is hydrogen, alkyl of 1 to 8 carbon atoms, benzo, chloro, or fluoro.

Other representative compounds are of formula:

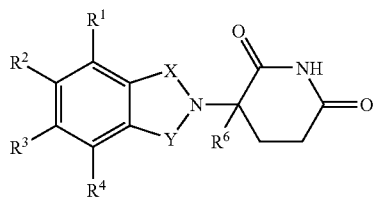

in which:
one of X and Y is C═O and the other of X and Y is C═O or CH$_2$;
(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;
R$^5$ is hydrogen, alkyl of 1 to 8 carbon atoms, or CO—R$^7$—CH(R$^{10}$)NR$^8$R$^9$ in which each of R$^7$, R$^8$, R$^9$, and R$^{10}$ is as herein defined; and
R$^6$ is alkyl of 1 to 8 carbon atoms, benzo, chloro, or fluoro.

Specific examples of the compounds are of formula:

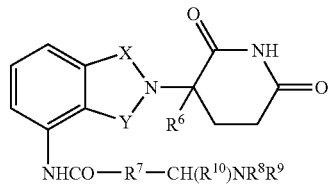

in which:
one of X and Y is C═O and the other of X and Y is C═O or CH$_2$;
R$^6$ is hydrogen, alkyl of 1 to 8 carbon atoms, benzyl, chloro, or fluoro;
R$^7$ is m-phenylene, p-phenylene or —(C$_n$H$_{2n}$)— in which n has a value of 0 to 4; each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$^1$CH$_2$CH$_2$— in which X$^1$ is —O—, —S— or —NH—; and R$^{10}$ is hydrogen, alkyl of 1 to 8 carbon atoms, or phenyl.

Other specific immunomodulatory compounds of the invention include, but are not limited to, 1-oxo-2-(2,6-dioxo-3-fluoropiperidin-3-yl)isoindolines and 1,3-dioxo-2-(2,6-dioxo-3-fluoropiperidine-3-yl)isoindolines such as those described in U.S. Pat. Nos. 5,874,448 and 5,955,476, each of which is incorporated herein by reference. Representative compounds are of formula:

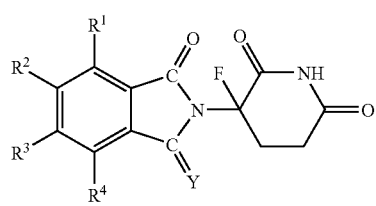

wherein:
Y is oxygen or H$^2$ and
each of R$^1$, R$^2$, R$^3$, and R$^4$, independently of the others, is hydrogen, halo, alkyl of 1 to 4 carbon atoms, alkoxy of 1 to 4 carbon atoms, or amino.

Other specific immunomodulatory compounds of the invention include, but are not limited to, the tetra substituted 2-(2,6-dioxopiperdin-3-yl)-1-oxoisoindolines described in U.S. Pat. No. 5,798,368, which is incorporated herein by reference. Representative compounds are of formula:

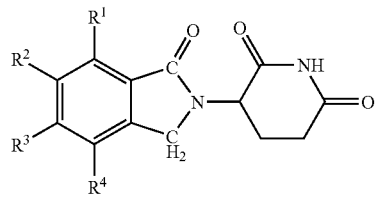

wherein each of R$^1$, R$^2$, R$^3$, and R$^4$, independently of the others, is halo, alkyl of 1 to 4 carbon atoms, or alkoxy of 1 to 4 carbon atoms.

Other specific immunomodulatory compounds of the invention include, but are not limited to, 1-oxo and 1,3-dioxo-2-(2,6-dioxopiperidin-3-yl)isoindolines disclosed in U.S. Pat. No. 6,403,613, which is incorporated herein by reference. Representative compounds are of formula:

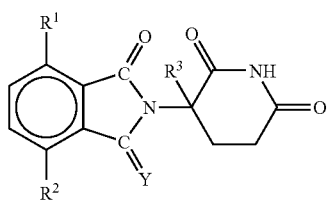

in which
Y is oxygen or H$_2$,
a first of R$^1$ and R$^2$ is halo, alkyl, alkoxy, alkylamino, dialkylamino, cyano, or carbamoyl, the second of R$^1$ and R$^2$, independently of the first, is hydrogen, halo, alkyl, alkoxy, alkylamino, dialkylamino, cyano, or carbamoyl, and R³ is hydrogen, alkyl, or benzyl.

Specific examples of the compounds are of formula:

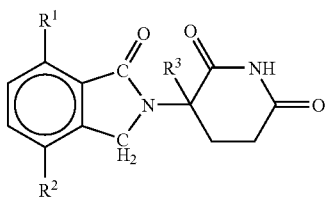

wherein a first of R¹ and R² is halo, alkyl of from 1 to 4 carbon atoms, alkoxy of from 1 to 4 carbon atoms, dialkylamino in which each alkyl is of from 1 to 4 carbon atoms, cyano, or carbamoyl;

the second of R¹ and R², independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and R³ is hydrogen, alkyl of from 1 to 4 carbon atoms, or benzyl. Specific examples include, but are not limited to, 1-oxo-2-(2,6-dioxopiperidin-3-yl)-4-methylisoindoline.

Other representative compounds are of formula:

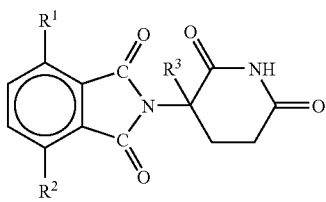

wherein:

a first of R¹ and R² is halo, alkyl of from 1 to 4 carbon atoms, alkoxy of from 1 to 4 carbon atoms, dialkylamino in which each alkyl is of from 1 to 4 carbon atoms, cyano, or carbamoyl;

the second of R¹ and R², independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and R³ is hydrogen, alkyl of from 1 to 4 carbon atoms, or benzyl.

Other specific immunomodulatory compounds of the invention include, but are not limited to, 1-oxo and 1,3-dioxoisoindolines substituted in the 4- or 5-position of the indoline ring described in U.S. Pat. No. 6,380,239 and co-pending U.S. application Ser. No. 10/900,270, filed Jul. 28, 2004, which are incorporated herein by reference. Representative compounds are of formula:

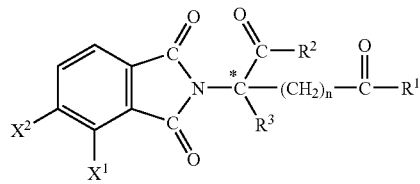

in which the carbon atom designated C* constitutes a center of chirality (when n is not zero and R¹ is not the same as R²); one of X¹ and X² is amino, nitro, alkyl of one to six carbons, or NH—Z, and the other of X¹ or X² is hydrogen; each of R¹ and R² independent of the other, is hydroxy or NH—Z; R³ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if X¹ is amino, and n is 1 or 2, then R¹ and R² are not both hydroxy; and the salts thereof.

Further representative compounds are of formula:

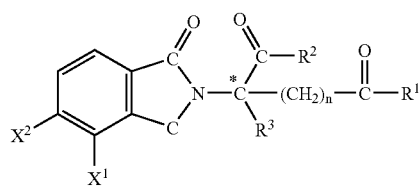

in which the carbon atom designated C* constitutes a center of chirality when n is not zero and R¹ is not R²; one of X¹ and X² is amino, nitro, alkyl of one to six carbons, or NH—Z, and the other of X¹ or X² is hydrogen; each of R¹ and R² independent of the other, is hydroxy or NH—Z; R³ is alkyl of one to six carbons, halo, or hydrogen; Z is hydrogen, aryl or an alkyl or acyl of one to six carbons; and n has a value of 0, 1, or 2.

Specific examples include, but are not limited to, 2-(4-amino-1-oxo-1,3-dihydro-isoindol-2-yl)-4-carbamoyl-butyric acid and 4-(4-amino-1'-oxo-1,3-dihydro-isoindol-2-yl)-4-carbamoyl-butyric acid, which have the following structures, respectively, and pharmaceutically acceptable salts, solvates, prodrugs, and stereoisomers thereof:

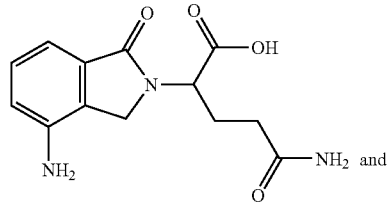 and

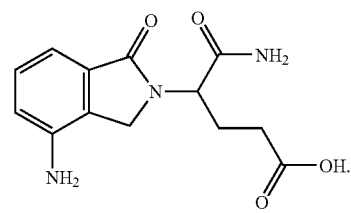

Other representative compounds are of formula:

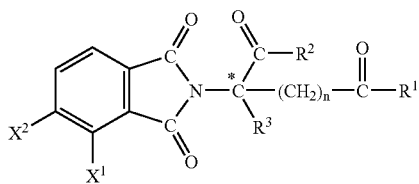

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl or acyl of one to six carbons; and n has a value of 0, 1, or 2; and the salts thereof.

Specific examples include, but are not limited to, 4-carbamoyl-4-{4-[(furan-2-yl-methyl)-amino]-1,3-dioxo-1,3-dihydro-isoindol-2-yl)}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptable salts, solvate, prodrugs, and stereoisomers thereof.

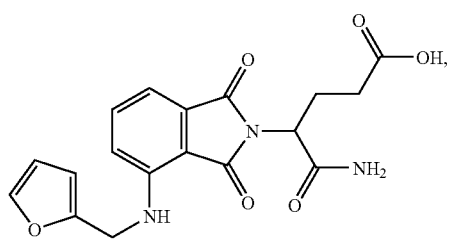

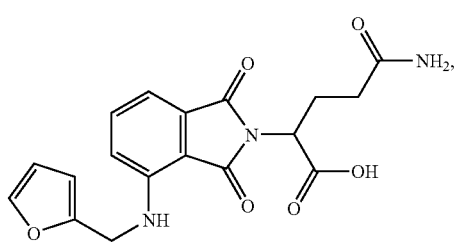

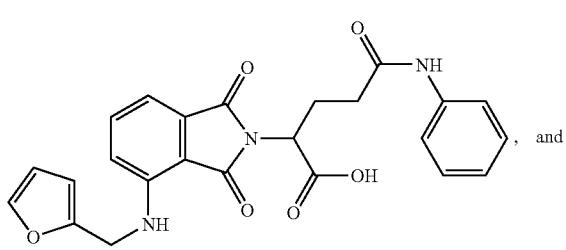, and

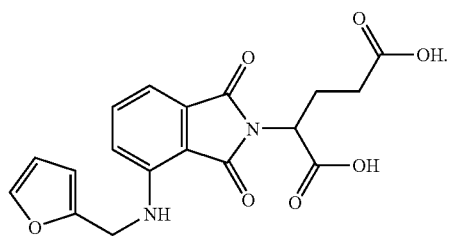

Other specific examples of the compounds are of formula:

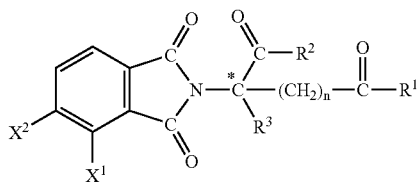

wherein:
one of $X^1$ and $X^2$ is nitro, or NH—Z, and the other of $X^1$ or $X^2$ is hydrogen;
each of $R^1$ and $R^2$, independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2; and
if —$COR^2$ and —$(CH_2)_nCOR^1$ are different, the carbon atom designated C* constitutes a center of chirality.

Other representative compounds are of formula:

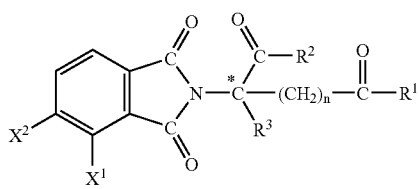

wherein:
one of $X^1$ and $X^2$ is alkyl of one to six carbons;
each of $R^1$ and $R^2$, independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2; and
if —$COR^2$ and —$(CH_2)_nCOR^1$ are different, the carbon atom designated C* constitutes a center of chirality.

Still other specific immunomodulatory compounds of the invention include, but are not limited to, isoindoline-1-one and isoindoline-1,3-dione substituted in the 2-position with 2,6-dioxo-3-hydroxypiperidin-5-yl described in U.S. Pat. No. 6,458,810, which is incorporated herein by reference. Representative compounds are of formula:

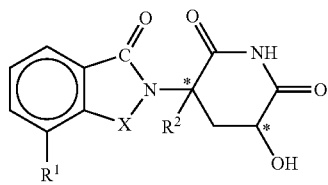

wherein:
the carbon atoms designated * constitute centers of chirality;
X is —C(O)— or —CH$_2$—;
R$^1$ is alkyl of 1 to 8 carbon atoms or —NHR$^3$;
R$^2$ is hydrogen, alkyl of 1 to 8 carbon atoms, or halogen; and
R$^3$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms,
benzyl, unsubstituted or substituted with alkyl of 1 to 8 carbon atoms, alkoxy of 1 to 8 carbon atoms, halo, amino, or alkylamino of 1 to 4 carbon atoms, or —COR$^4$ in which
R$^4$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms, or
benzyl, unsubstituted or substituted with alkyl of 1 to 8 carbon atoms, alkoxy of 1 to 8 carbon atoms, halo, amino, or alkylamino of 1 to 4 carbon atoms.

All of the compounds described can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

Compounds used in the invention may be small organic molecules having a molecular weight less than about 1,000 g/mol, and are not proteins, peptides, oligonucleotides, oligosaccharides or other macromolecules.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.4 Methods of Treatment and Prevention

This invention encompasses methods of treating and/or preventing (e.g., prophylactic treatment such as vaccination) of various disorders using the dosing regimen involving an immunomodulatory compounds of the invention as described herein.

In one embodiment, this invention encompasses treatment or prevention of cancer. Examples of cancer that can be treated or prevented using methods of the invention include those described in Section 5.1.2, above. In some embodiments, cancers to be treated or prevented using methods of the invention are metastatic. In other embodiment, specific cancers that can be treated or prevented using methods of the invention are sarcoma, carcinoma, melanoma, lymphoma and leukemia.

In another embodiment, this invention encompasses methods of vaccinating against cancer by reducing the inhibition of anti-tumor immune response in a subject (e.g., a human) comprising administering to the subject an immunomodulatory compound of the invention prior to the administration of a cancer vaccine. This invention also encompasses methods of enhancing immune response to a cancer vaccine in a subject comprising administering to the subject an immunomodulatory compound of the invention prior to the administration of a cancer vaccine. Examples of cancer vaccines that can be used in connection with methods of the invention include those listed in Tables 1-4. In specific embodiment, cancers against which vaccination is performed are sarcoma, carcinoma, melanoma, lymphoma and leukemia. In another specific embodiment, the cancer vaccine is an antigen modified denritic cell vaccine, a peptide vaccine, a whole tumor cell vaccine, or a viral vector vaccine.

In another embodiment, this invention also encompasses treatment or prevention of an infectious disease. Examples of infectious diseases that can be treated or prevented using methods of the invention are described in Section 5.1.2, above. In some embodiments, infectious diseases that can be treated or prevented using methods of the invention include those caused by viruses, bacteria, fungi, and parasites.

In another embodiment, this invention encompasses methods of vaccinating against an infectious disease by reducing the inhibition of immune response in a subject (e.g., a human) comprising administering to the subject an immunomodulatory compound of the invention prior to the administration of a vaccine against an infectious disease. This invention also encompasses methods of enhancing immune response to a vaccine against an infectious disease in a subject comprising administering to the subject an immunomodulatory compound of the invention prior to the administration of the vaccine. Examples of infectious diseases against which a subject can be vaccinated according to methods of the invention are described in Section 5.1.1, above. In a specific embodiment, infectious diseases are those caused by viruses, bacteria, fungi, and parasites. In a specific embodiment, the vaccine against an infectious disease is hepatitis B vaccine.

5.5 Methods of Administration

Methods encompassed by this invention comprise administering one or more immunomodulatory compounds, or a pharmaceutically acceptable salt, solvate, stereoisomer, or prodrug thereof, to a subject (e.g., a human) prior to the exposure to or administration of an immunogen or an allergen.

Any route of administration may be used. For example, an immunomodulatory compound can be orally, parenterally, transdermally, rectally, sublingually, mucosally, or nasally administered. In addition, an immunomodulatory compounds can be administered in a form of pharmaceutical composition and/or unit dosage form. Suitable dosage forms include, but are not limited to, capsules, tablets (including rapid dissolving and delayed release tablets), powder, syrups, oral suspensions and solutions for parenteral administration. Pharmaceutical compositions may contain one of more pharmaceutically acceptable excipients. See, e.g., Rowe et al., Handbook of Pharmaceutical Excipients, 4th Ed. (2003), entirety of which is incorporated herein by reference. In addition, an immunomodulatory compound of the invention may be included in a kit, which may comprise an immunogen or an allergen, one or more other active ingredients, and devices and directions for administration. Other ingredients (e.g., immunogen, allergen, and other active ingredients) may be included in the same formulation with the immunomodulatory compound of the invention, or in separate formulations.

The specific amount of the agent will depend on the specific agent used, the type of disease or disorder being treated or managed, and the amount(s) of an immunomodulatory compound of the invention and any optional additional agents concurrently administered to the patient. Typical dosage forms of the invention comprise an immunomodulatory compound of the invention or a pharmaceutically acceptable salt, solvate, stereoisomer, or prodrug thereof in an amount of from about 0.001 to about 150 mg. In particular, dosage forms comprise an immunomodulatory compound of the invention or a pharmaceutically acceptable salt, solvate, stereoisomer, or prodrug thereof in an amount of about 0.001, 0.01, 0.1, 1, 2, 5, 7.5, 10, 12.5, 15, 17.5, 20, 25, 50, 100, 150 or 200 mg. In a particular embodiment, a dosage form comprises 4-(amino)-2-(2,6-dioxo(3-piperidyl))-isoindoline-1,3-dione in an amount of about 0.001, 0.01, 0.1, 1, 2, 5, 10, 25 or 50 mg.

In some embodiments, this invention encompasses administration of racemic mixture, optically pure (R)-isomer, or optically pure (S)-isomer of 4-(amino)-2-(2,6-dioxo(3-piperidyl))-isoindoline-1,3-dione. In one specific embodiment, the racemic 4-(amino)-2-(2,6-dioxo(3-piperidyl))-isoindoline-1,3-dione is administered at an amount of 1, 2, 5, 10, or 25 mg per day. As (S)-isomer of 4-(amino)-2-(2,6-dioxo(3-piperidyl))-isoindoline-1,3-dione is reported to have a higher potency than the racemic mixture, a lower dose can be given when (S)-isomer is used. For examples, (S)-4-(amino)-2-(2,6-dioxo(3-piperidyl))-isoindoline-1,3-dione can be administered at an amount of 0.01, 0.1, 1.2.5, 5, or 10 mg per day. (R)-isomer of 4-(amino)-2-(2,6-dioxo(3-piperidyl))-isoindoline-1,3-dione can be administered at an amount comparable to the racemic mixture.

In a specific embodiment, a dosage form comprises 3-(4-amino-1-oxo-1,3-dihydro-isoindol-2-yl)-piperidine-2,6-dione in an amount of about 0.001, 0.01, 0.1, 1, 5, 10, 25 or 50 mg. Typical dosage forms comprise the second active ingredient in an amount of 1 µg to about 1000 mg, from about 0.01 to about 500 mg, from about 0.1 to about 350 mg, or from about 1 to about 200 mg. This invention also encompasses the use of racemic mixture, (S)-isomer, and (R)-isomer of 3-(4-amino-1-oxo-1,3-dihydro-isoindol-2-yl)-piperidine-2,6-dione. Typically, racemic 3-(4-amino-1-oxo-1,3-dihydro-isoindol-2-yl)-piperidine-2,6-dione can be administered at an amount of 1, 5, 10, 15, 25, or 50 mg per day. Optical isomers also can be administered at an amount comparable to racemic mixture. Doses can be adjusted depending on the type of disease or disorder being treated, prevented or managed, and the amount(s) of an immunomodulatory compound of the invention and any optional additional agents concurrently administered to the patient, which are all within the skill of the art.

6. EXAMPLES

6.1 Effects of IMiDs on Regulatory T Cells

An assay in which the ability of isolated $T_{reg}$ to suppress anti-CD3 mAb activated CD4+CD25− cells was performed. Results showed that pre-incubation of $T_{reg}$ with 4-(amino)-2-(2,6-dioxo(3-piperidyl))-isoindoline-1,3-dione (Actimid™) and 3-(4-amino-1-oxo-1,3-dihydro-isoindol-2-yl)-piperidine-2,6-dione (lenalidomide), but not thalidomide, inhibits the suppressive function of these cells. The inhibition of T regulatory cell function and production by these compounds was shown to be not due to any cytotoxic or apoptotic effects of the IMiDs on the cells, but the inhibition of function was associated with a decrease in FOXP3 expression in CTLA4+ CD25$^{high}$CD4+ cells.

6.1.1 Effects on $T_{reg}$ Function

Figure 2A:
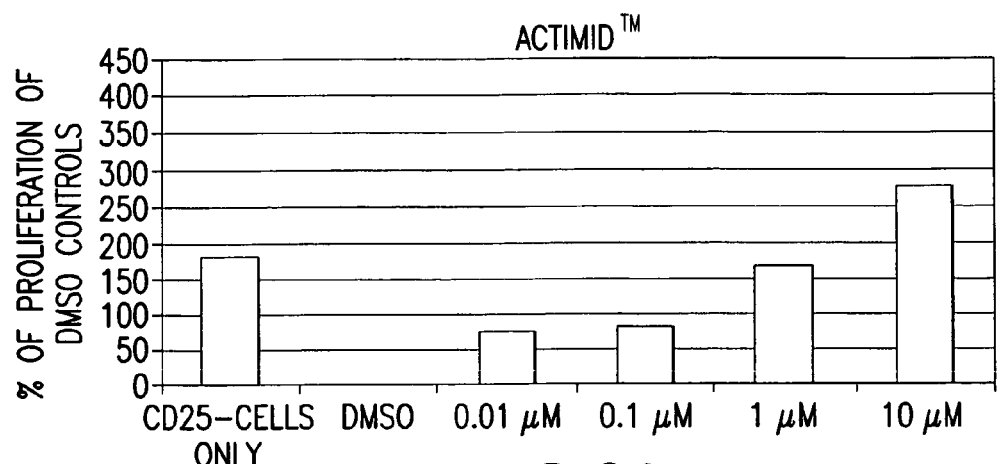
FIG. 2A illustrates the effects of 4-(amino)-2-(2,6-dioxo (3-piperidyl))-isoindoline-1,3-dione on the function of regulatory T cells.
Figure 2B:
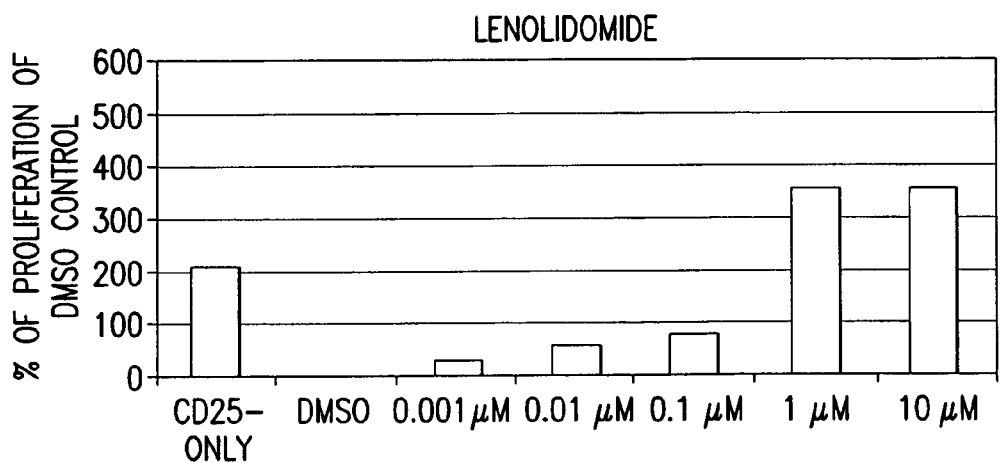
FIG. 2B illustrates the effects of 3-(4-amino-1-oxo-1,3-dihydro-isoindol-2-yl)-piperidine-2,6-dione on the function of regulatory T cells.
Figure 2C:
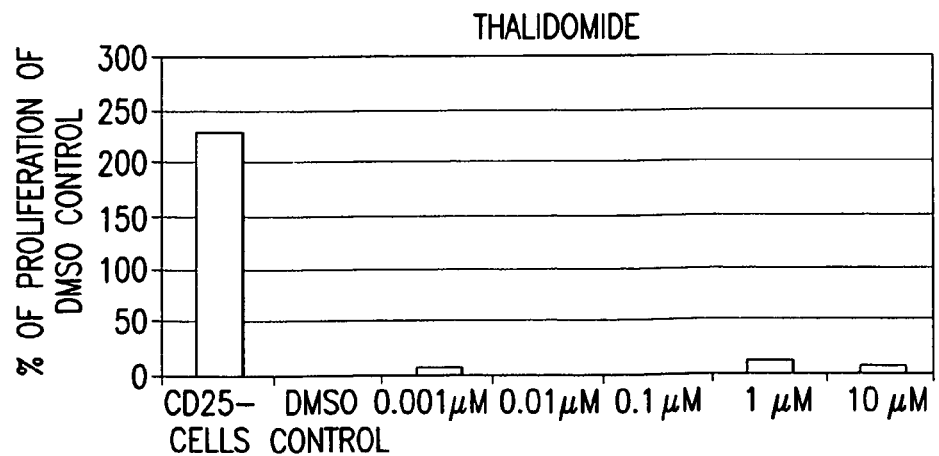
FIG. 2C illustrates the effects of thalidomide on the function of regulatory T cells.

Regulatory T cells were isolated by the Dynal T regulatory cell isolation kit, and treated for 24 hours with varying concentrations of an immunomodulatory compound (Actimid™ or lenalidomide) or DMSO. The cells were washed and incubated at a 1:2 ratio with CD25$^-$CD4$^+$ cells, which were also isolated by the Dynal T regulatory cell isolation kit. Results were expressed as the mean % change in proliferation compared to the cpms obtained from DMSO treated CD25$^+$ cells incubated with CD25$^-$ cells. As shown in FIG. 2, pre-treatment of CD25$^+$CD4$^+$ cells with the IMiDs tested significantly increased the proliferation of CD25$^-$ cells in the presence of CD25$^+$CD4$^+$ cells as compared to the DMSO treated CD4$^+$CD25$^+$ cells. Thalidomide showed little effect under these assay conditions. The results suggest that the IMiDs tested reduce or inhibit the suppressive activity of regulatory T cells.

6.1.2 Effects on Foxp3 Expression

CD4$^+$CD25$^+$ cells were incubated for 24 hours with varying concentrations of DMSO, Actimid™, lenalidomide, or thalidomide and then washed twice with RPMI medium. Cells were stained with CD152-PE, CD4-PERCP, and CD25-APC. Intracellular Foxp3 staining and CD152 staining were carried out after permeabilizing the CD4$^+$ CD25$^+$ cells. Results were expressed as percentage of expression of Foxp3 in the CD4$^+$CD25$^+$ population or the CD4$^+$CD25$^-$ population. As shown in FIG. 3, cells pre-treated with the IMiDs showed inhibition of Foxp3 expression, while DMSO and thalidomide showed little effects. The results show that the inhibition of $T_{reg}$ cells by the IMiDs tested may be associated with the compounds' ability to inhibit Foxp3 expression.

6.1.3 Effects on Level of $T_{reg}$ Cells

PBMCs were treated with 150 U/ml of IL-2. Some of the cultures were also treated with Actimid™ or lenalidomide. Cells were stained with CD25-FITC/CD152-PE/CD4-PerCP/NKG2D-APC and analyzed using a FACSCalibur. As shown in FIG. 4, levels of CD4, CD25high, CD52high expressing cells are reduced in groups pre-treated with an IMiD as compared to the untreated group. The results suggest that the IMiDs of the invention also decrease the levels of regulatory T cells or inhibits the proliferation of such cells.

6.2 Effects on Acquired Antibody Resistance

Rituximab-resistant cell lines (RRCL) were generated by chronic exposure of Raji cells to escalating doses of rituximab alone (2R) or along with human complement (4RH). Functional assays including antibody-dependant cellular cytotoxicity (ADCC) and complement-mediated cytotoxicity (CMC) were performed to demonstrate resistance to rituximab. To study the effects of lenalidomide-priming of PBMC's against RRCL, peripheral blood mononuclear cells from healthy donors were cultured with either DMSO or lenalidomide (at final concentrations of 10 or 20 µg/ml), with or without IL-2 (20 IU/ml), over a 5-day period at 37° C., 5% $CO_2$. Parental Raji, and RRCL (2R and 4RH) were labeled with $^{51}$Cr and exposed to either rituximab or trastuzumab (Isotype control at 20 µg/ml) in the presence of an IMiD or control stimulated-PBMCs (Effector:Target ratio of 40:1). $^{51}$Cr release was measured and the percentage of lysis was calculated. Statistical differences were analyzed by chi-square test.

In vitro exposure of PBMC to IMiD+/−IL-2 improved rituximab-associated ADCC in RRCL. Exposure of PBMC to IMiD+/−IL-2 for 5 days led to a statistically significant increase in rituximab-mediated ADCC in 2R cells [IMiD mean % lysis 26.9+/−1.18%] [IMiD+IL-2 mean % lysis 38.4+/−4.14%] when compared to control-stimulated PBMC's [mean % lysis 17.6+/−5.6%]. Similar effects were observed in 4RH cells. The mean % of lysis by ADCC for combination IMiD/IL-2 exposed PBMC's on 4RH cells was found to be highest at 38.4+/−4.1%, as compared to IMiD (mean % lysis 26.5+/−1.83%) or vehicle exposed PBMC's (mean % lysis 17.6+/−5.69%) (P=0.01). These results suggest that modulation (e.g., PBMC-priming) of the immune system by the IMiD of the invention (+/−IL-2) improves rituximab anti-tumor activity and may partially overcome rituximab resistance in RRCL via augmentation of ADCC.

6.3 Effects on Growth Arrest and Apoptosis

Direct effects of IMiDs on NHL tumor cells were tested by treating Raji cells with IMiDs alone, or in combination with anti CD20 antibodies B1 or rituxan. IMiD 1 alone caused up to 40% inhibition of proliferation at 10 µM in Raji cells, which corresponded to G1 arrest. In combination with B1, Actimid™ showed a small additive effect at 10 µM, while lenalidomide effects were minimal up to 10 µM. In combination with rituxan, Actimid™ showed a slight additive effect at 10 µM, and lenalidomide showed the same at 50 µM.

A co-culture assay of PBMC and NHL tumor cells were developed as an in vitro model of tumor-host immune system interaction, to further explore the anti-tumor potential of IMiDs in NHL cells. This assay is non-radioactive and flow cytometry based. Using Raji and PBMC, it was shown that pre-treatment of PMBC with an IMiD can enhance the PBMC activity in inducing Raji cell apoptosis in a dose dependent manner. In addition, it was shown that pre-treatment of Raji cells with an IMiD can further enhance the apoptosis induced by PBMC pre-treated with an IMiD. These results suggest that the IMiDs of the invention directly induce NHL tumor cell growth arrest and effectively enhance tumor cell apoptosis induced by PBMC.

6.4 Effects on HSC Expansion

The ability of IMiDs to enhance the expansion of hematopoietic stem cells (HSC) ex vivo in combination with growth factors were tested. It was shown that the IMiDs of the invention dramatically enhance the expansion of CD34+ cells in a serum-free system, achieving up to 100-fold expansion after 14 days in culture. In addition, the IMiDs of the invention enabled a preferential expansion of CD34+CD38− cells, a more immature phenotype.

IMiDs showed similar activities on HSC from all sources tested: bone marrow, cord blood and peripheral blood (steady-state or G-CSF-mobilized). It was also shown that IMiDs can efficiently expand CD34+ cells isolated from frozen cord blood units.

Global gene expression (Affymetrix) analysis of IMiDs-expanded CD34+ cells revealed that the IMiDs of the invention modulate several genes involved in cell differentiation, cell adhesion and cell self-renewal. The IMiDs of the invention also upregulated many genes involved in immune responses and antigen presentation.

6.5 Effects on T Cell Differentiation

Effects of IMiDs on T cell differentiation were investigated using various methods. It was demonstrated that, in combination with anti-CD3 stimulation, the IMiD of the invention directly increases expression of Th1 transcription factor T-bet via enhanced T-bet RNA transcription at 4 hours after stimulation. A concomitant decrease in expression of Th2 transcription factor GATA-3 was also observed. The regulation of two key transcription factors by the IMiD favors Th1 differentiation of human naive CD4$^+$ T cells. Enhancement of T-bet by the IMiD results in increased tyrosine phosphorylation of T-bet, increased expression of IL-12Rβ2, and increased IFN-γ production, compared to treatment with anti-CD3 alone.

A similar effect of the IMiD on T-bet and GATA-3 was also observed in differentiated human Th2 cells in vitro under Th2 polarizing condition. The intracellular cytokine staining of IL-4 and IFN-γ on re-stimulated Th2 cells showed that the IMiD reduced the number of IL-4 producing cells and increased the number of IFN-γ producing cells in the presence of plate bound anti-CD3 antibody. The effect of the IMiD on polarized Th2 cells includes reversal of Th2 cell differentiation and enforcement of IFN-γ expression in IL-4 positive cells, which is greatly enhanced by addition of exogenous IL-12. These results suggest that the IMiDs of the invention not only preferentially induce Th1 immune response by enhancing T-bet, but also inhibit Th2 lineage commitment by reducing GATA-3 expression.

6.6 Effects on T Cell Activation

The Gab proteins, including Gab1, Gab2 and Gab3 comprise a growing family of phospho-tyrosine regulated scaffolding molecules involved in RTK signal transduction. Phosphorylation of Gab1 in B cells is associated with P13-kinase activity and cell proliferation. While Gab1 is expressed in B cells, only Gab2 is expressed in T cells. Although Gab2 is tyrosine phosphorylated upon TCR activation by ZAP-70, it functions as a negative regulator of TCR signaling via a Shp-2 dependent mechanism. Overexpression of Gab2 in T cells results in the inhibition of IL-2 production (Yamasaki et al., *J. Biol. Chem.*, 2001). The effect of lenalidomide on Gab2 phosphorylation and activation in anti-CD3/CD28 stimulated Jurkat T cells was examined. Lenalidomide inhibited Gab2 phosphorylation dose-dependently (with approximately 50% inhibition at about 1 µM) in a manner that correlated with T cell costimulation and enhancement of IL-2 production. The results show that the mechanism of action of lenalidomide is therefore consistent with inhibition of phosphorylation of Gab2 in anti-CD3/CD28-stimulated T cells.

6.7 Effects on γδ T Cells 6.7.1 Materials and Methods

Phenotyping of PBMC Preparations Stimulated with IL-2 and IPP±IMiDs:

PBMC preparations were obtained and treated weekly with IL-2 and IPP (150 units/ml and 10 uM respectively). Expression of δγ TCR and NKG2D were measured by FACS over a period of three weeks.

Generation of γδ T Cells:

PBMC preparations were treated with IL-2 (150 units/ml) and IPP (25 uM) weekly. Cultures were split and replenished weekly with fresh IL-2 and IPP and % γδ TCR+ve cells determined by FACS. After 3-4 weeks γδ T cells were purified by negative magnetic separation using CD4+ and CD8+ Dynalbeads and maintained in IL-2.

Measurement of Cytokine Production in Purified γδ T Cells and Fresh γδ Cells in PBMC Preparations:

Purified γδ T cells were stimulated with IPP±IMiDs (10 g/mL) or with the MM cell line RPMI-8226 (±IMiDs (10 g/mL)) in 24 well plates and were incubated 8-72 hours. Cell-free supernatants were collected and stored at −70° C. until assayed by ELISA. IFN-γ, TNF-α and IL-2 were measured by ELISA (BD pharmingen). For fresh δγ preps, PBMCs were stimulated with plate bound anti-CD3 (1.25 µg/ml) for 48 hours and the expression of TNF-α, IFNγ, IL-2 and IL-4 were measured by intracellular FACS on cells stained for γδ TCR.

Measurement of Apoptosis in δγ Cells:

Gamma delta T cells were treated with a single dose of 25 μM IPP and weekly with 150 U/ml of IL-2 for 4 weeks and 3 days. Cells were then either left untreated or treated with Actimid™, IPP or Actimid™ and IPP. Apoptosis was assessed by staining of cells with annexin V PE and 7-AAD at various time points and analysis using a FACSCalibur.

Cytotoxicity Assays:

Gamma delta T cells were treated with a single dose of 25 μM IPP and weekly with 150 U/ml of IL-2 for 3 weeks and 1 day. RPMI-8226 target cells were incubated overnight with 50 μM pamidronate then treated with 3MBq 51Cr. Target, and effector cells were incubated at different ratios and chromium release was assayed after 4 hours. To determine the effects of Actimid™, the compound was either included in the 22 day preincubation before the assay and in the chromium release step, or was included during the chromium release assay.

6.7.2 Effects on the Expression of γδ T Cells and NKG2D

PBMCs were treated with a single dose of 25 μM IPP and then weekly with 150 U/ml of IL-2. In addition, some cultures were treated with 10 μM Actimid™ or lenalidomide. IL-2 treated cells were stained with CD25 FITC/CD4 PE/CD3 PerCP/NKG2D APC, and IL-2 plus IPP treated cells were stained with δγ TCR FITC/alpha beta TCR PE/CD3 PerCP/NKG2D APC and analysed using a FACSCalibur.

As shown in FIG. 5, cells treated with an immunomodulatory compound of the invention exhibited higher γδ T cells and NKG2D expression. The results show that immunomodulatory compounds of the invention enhance the expression of γδ T cells and NKG2D in PMBCs activated with IL-2 and IPP.

6.7.3 Effects of Apoptosis of γδ T Cells

Gamma delta T cells were treated with a single dose of 25 μM IPP and weekly with 150 U/ml of IL-2 for 31 days. Cells were then either left untreated or treated with Actimid™, IPP, or Actimid™ and IPP in combination. Apoptosis was assessed by staining of cells with annexin V PE and 7-AAD at the stated time points and analysis using a FACSCalibur. Annexin V PE negative/7-AAD negative cells are designated live, annexin V PE positive/7-AAD negative early apoptotic, annexin V PE positive/7-AAD positive late apoptotic and annexin V PE negative/7-AAD positive dead.

As shown in FIG. 6, Actimid™ offered protection against apotosis in γδ T cells with or without IPP. The results suggest that immunomodulatory compounds of the invention protect against apotosis of γδ T cells.

6.7.4 Effects on Cytokine Production by γδ T Cells

The effects of Actimid™ on IFN-γ, TNF-α, and IL-4 were examined in freshly prepared γδ T cells and γδ T cell lines stimulated with IPP. As shown in FIG. 7A, Actimid™ enhanced the production of both IFN-γ and TNF-α in TCR γδ cells from within a freshly prepared PMBC population. In addition, as shown in FIG. 7B, Actimid™ enhanced the production of IFN-γ, but not IL-4, in γδ T cells stimulated with IPP. The results show that immunomodulatory compounds of the invention stimulate the production of IFN-γ and TNF-α, but not IL-4.

6.7.5 Effects on IFN-γ Production in Response to Varying Tumor to γδ T Cells Ratio Tumor cells pre-incubated with (FIG. 8B) or without (FIG. 8A) pamidronate were incubated with δγ T cells at different tumor (RPMI-8226 MM) to γδ T cells ratios as indicated in FIG. 8. Some of the cells were further treated by Actimid™. Intracellular IFN-gamma production was measured by flow cytometry.

As shown in FIGS. 8A and 8B, Actimid™ augmented IFN-γ production by γδ T cells. IFN-γ production increased with increasing tumor to γδ T cells ratio. The results show that immunomodulatory compounds of the invention enhance the production of IFN-γ by γδ T cells, and the effects increase in response to increasing tumor to γδ T cells ratio.

6.7.6 Effects on Cytotoxicity of γδ T Cells

Gamma delta cells were treated with a single dose of 25 μM IPP and weekly with 150 U/ml of IL-2 for 22 days. RPMI-8226 target cells were incubated overnight with 50 μM pamidronate, then treated with 3 MBq 51 Cr. Target and effector cells were incubated at various ratios with fresh Actimid™ and chromium release assayed after 4 hours. Actimid™ was also added to some wells for the 22 day pretreatment with IL-2 and IPP (FIG. 9A) or just for the 4 hr chromium release assay (FIG. 9B).

As shown in FIG. 9, the addition of Actimid™ during either the pretreatment or the chromium release assay enhanced the cytotoxicity of γδ T cells toward RPMI-8226 MM cell lines, although a better effect was observed with the addition of Actimid™ during the pretreatment of period. The results suggest that immunomodulatory compounds of the invention enhance the cytotoxicity of γδ T cells toward tumor cells, and the effects may be improved by pretreating the tumor cells with the compounds of the invention.

6.8 Effects on Invariant NKT Cells

The establishment of highly purified primary invariant NKT (iNKT) cell lines from health donors and multiple myeloma (MM) patients has been tested, and the effects of IMiD 2 on iNKT cells were further explored. iNKT cells derived from peripheral blood or bone marrow mononuclear cells were enriched with anti-TCRVα 24 mAb or anti-6B11 mAb and further expanded by several rounds of stimulation with α-GalCer-loaded dendritic cells. Phenotype analysis confirmed 95% purity in expanded iNKT cell lines. No significant phenotypic difference was observed in iNKT cells between healthy donors and MM patients.

Majority of iNKT cells expressed CD161 and CD28, whereas CD56 expression was at very low level. Following anti-CD3 or α-GalCer-loaded dendritic cells stimulation, iNKT cells showed strong proliferative activity as measured by $^3$H-TdR incorporation assay and production of IFN-γ measured by ELISA.

Next, the effects of IMiD 2, which is known to enhance T cell costimulation and NK cell activity, on iNKT cells were evaluated. From the tests, it was observed that IMiD 2 enhances anti-CD3 mediated proliferation of expanded iNKT cells by 1.4 fold, and the enhanced expression and fluorescent intensity of CD25 (MFI 68.6 versus 28.5) on iNKT cells treated with IMiD 2 compare to untreated iNKT cells. Additionally, compared to the control group stimulated with α-GalCer-loaded dendritic cells alone, IMiD 2 plus α-GalCer-loaded DC also enhanced the production of IL-2. These results provide the preclinical feasibility and rationale to clinically evaluate the efficacy of adoptive transfer of iNKT cells in MM. Additionally, the results demonstrate the ability of the IMiDs of the invention to augment the immunoreactivity of iNKT cells, suggestive of their use in enhancing iNKT cell mediated immunotherapy in myeloma.

6.9 Use with Hepatitis B Vaccine

A two-center, randomized, double-blind, placebo-controlled trial is designed. A single dose of Hepatitis B vaccine is administered to subjects. An IMiD or placebo is administered to 64 patients for 7 days prior to and 7 days after the vaccine. Collection of blood samples for immune analysis is performed prior to the initiation of the IMiD administration, at the time of vaccination, and 7, 14, and 28 days after vaccination. Safety assessments is performed at day 14, the last day of study drug.

Subjects may opt for 2nd and 3rd doses of vaccine in order to complete the usual course of hepatitis B vaccination. Opting for additional vaccinations is not a requirement of this study. Patients opting to receive the second (day 28) and 3rd (6 month) vaccination may have their blood samples collected prior to the 2nd and 3rd and 1 month after 3rd vaccination. The 28 day blood draw serves as the blood draw prior to the 2nd dose of vaccine. The blood draws one month after the 2nd and 3 dose are not required for subjects wishing to receive the 2nd and 3rd dose of vaccine.

The effect of the IMiD on the response to hepatitis B vaccine in subjects with plasma cell dyscrasias, as measured by change in antibody titer against hepatitis B surface antigen (HbSAg), can be determined following the above procedures. In addition, serum and blood cells can be collected to: a) assess the development of T cell responses against HbSAg following vaccination; b) identify phenotypic changes in peripheral blood cells following the IMiD administration especially with regard to CD3, CD4, CD8 T cells, and NK and NKT cells; and c) determine changes in gene expression profile of immune cells before and after the treatment of the IMiD using micro array protocols.

6.10 $T_{Reg}$ Cell Phenotyping and Functional Analyses from Patients Undergoing Lenalidomide Treatment Patients with any malignancy which are selected for lenalidomide treatment in are asked to participate in this study. The cycle of dosing for the patients selected for lenalidomide treatment is 3 weeks of dosing with 25 mg lenalidomide daily, followed by 1 week without dosing, followed by three more weeks of dosing, in repeated cycles. Forty ml samples of blood are collected into heparin tubes and 5 mls into serum tubes at time points from 1 hour to 24 hrs before the first administration of lenalidomide (25 mg/dose) and at 21 days and 49 days after dosing.

The blood in the heparin tubes is layered onto histopaque and spun for 25 minutes at 600 g to separate the buffy coat layer. The buffy coat containing the peripheral blood mononuclear cells and malignant haematogical cells is isolated. The cells isolated are subjected to the following procedures:

6.10.1 Phenotype Analysis Using a FACscalibur Machine

Dominant phenotypes of the PBMCs freshly isolated from each patient are analyzed, and the percentage of cells in the patients that are of a regulatory T cell phenotype (CD4$^+$ CD25$^+$ positive cells, staining positive also for FOXP3 and CTLA-4) is measured.

6.10.2 Isolation of CD4$^+$CD25$^+$ Cells from the Patients PBMCs

CD4$^+$CD25$^+$ cells and CD4$^+$CD25$^-$ cells are isolated from the patients' PBMCs using standard magnetic bead kits (Invitrogen). The ability in-vitro of the CD4$^+$CD25$^+$ cells to inhibit the proliferation of CD4$^+$CD25$^-$ cells, upon stimulation with anti-CD3, is assessed.

6.10.3 Analysis of Serum

Serums are analysed for TGF-beta, IL-10, IL-4, IL-6, IFN-γ and TNF-α concentrations, using methods described herein as well as those well-known in the art.

All of the references cited herein are incorporated by reference in their entirety. While the invention has been described with respect to the particular embodiments, it will be apparent to those skilled in the art that various changes and modifications may be made without departing from the spirit and scope of the invention as recited by the appended claims.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of eliciting an enhanced immune response from an immunogen in a subject comprising administering to the subject an immunomodulatory compound prior to initial introduction of the immunogen as a vaccine to the subject, wherein the immunomodulatory compound is a compound of formula I, or a pharmaceutically acceptable salt or stereoisomer thereof:

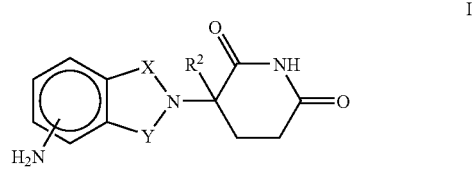

wherein:
one of X and Y is C═O, the other of X and Y is C═O or CH$_2$;
R$^2$ is hydrogen or lower alkyl.

2. The method of claim 1, wherein the immunomodulatory compound is administered from about 10 days to about 12 hours prior to the introduction of an immunogen.

3. The method of claim 2, wherein the immunomodulatory compound is administered from about 7 days to about 12 hours prior to the introduction of an immunogen.

4. The method of claim 3, wherein the immunomodulatory compound is administered from about 5 days to about 1 day prior to the introduction of an immunogen.

5. The method of claim 4, wherein the immunomodulatory compound is administered from about 3 days to about 1 day prior to the introduction of an immunogen.

6. The method of claim 1, which further comprises a second administration of an immunomodulatory compound after the introduction of an immunogen.

7. The method of claim 6, wherein the immunomodulatory compound is administered from about 12 hours to about 10 days after the introduction of an immunogen.

8. The method of claim 7, wherein the immunomodulatory compound is administered from about 12 hours to about 7 days after the introduction of an immunogen.

9. The method of claim 8, wherein the immunomodulatory compound is administered from about 1 day to about 5 days after the introduction of an immunogen.

10. The method of claim 9, wherein the immunomodulatory compound is administered from about 1 day to about 3 days after the introduction of an immunogen.

11. The method of claim 1, wherein the immunogen comprises a tumor antigen.

12. The method of claim 1, wherein the immunomodulatory compound is 4-(amino)-2-(2,6-dioxo(3-piperidyl))-isoindoline-1,3-dione.

13. The method of claim 12, wherein the immunomodulatory compound is enantiomerically pure.

14. The method of claim 1, wherein the immunomodulatory compound is 3-(4-amino-1-oxo-1,3-dihydro-isoindol-2-yl)-piperidine-2,6-dione.

15. The method of claim 14, wherein the immunomodulatory compound is enantiomerically pure.

* * * * *